(12) United States Patent
Kameoka et al.

(10) Patent No.: US 8,586,316 B2
(45) Date of Patent: Nov. 19, 2013

(54) METHODS FOR DETECTING MOLECULE-MOLECULE INTERACTIONS WITH A SINGLE DETECTION CHANNEL

(75) Inventors: Jun Kameoka, College Station, TX (US); Nan Jing, Fishkill, NY (US); Mien-chie Hung, Houston, TX (US); Chao-Kai Chou, Houston, TX (US)

(73) Assignees: The Board of Regents of the University of Texas System, Austin, TX (US); The Texas A&M University System, College Station, TX (US)

( * ) Notice: Subject to any disclaimer, the term of this patent is extended or adjusted under 35 U.S.C. 154(b) by 193 days.

(21) Appl. No.: 12/866,658

(22) PCT Filed: Feb. 9, 2009

(86) PCT No.: PCT/US2009/033577
§ 371 (c)(1),
(2), (4) Date: Feb. 10, 2011

(87) PCT Pub. No.: WO2009/100442
PCT Pub. Date: Aug. 13, 2009

(65) Prior Publication Data
US 2012/0070846 A1 Mar. 22, 2012

Related U.S. Application Data

(60) Provisional application No. 61/026,978, filed on Feb. 7, 2008.

(51) Int. Cl.
*G01N 33/53* (2006.01)
*G01N 33/536* (2006.01)
*G01N 21/76* (2006.01)

(52) U.S. Cl.
USPC ............................. 435/7.1; 436/537; 436/172

(58) Field of Classification Search
None
See application file for complete search history.

(56) References Cited

U.S. PATENT DOCUMENTS

| 6,355,420 | B1 | 3/2002 | Chan et al. ........................ 435/6 |
| 6,613,581 | B1 | 9/2003 | Wada et al. .................... 436/518 |
| 2004/0007675 | A1 | 1/2004 | Gillispie et al. ............ 250/458.1 |
| 2005/0084612 | A1* | 4/2005 | Yang et al. ..................... 427/269 |
| 2005/0201660 | A1 | 9/2005 | Grot et al. ........................ 385/12 |
| 2006/0291772 | A1 | 12/2006 | Haiml et al. ..................... 385/16 |
| 2010/0304358 | A1* | 12/2010 | Nie et al. ........................... 435/5 |

FOREIGN PATENT DOCUMENTS

WO   WO 2006/020914   2/2006

OTHER PUBLICATIONS

"Fluorescence Correlation Spectroscopy: Theory and Applications," Chapter 5, Rigler and Elson (Eds.), Springer, Berlin, Germany, 2001.
"Fluorescence SpectraViewer", available at Invitrogen website located at probes.invitrogen.com/resources/spectraviewed, 2011.
"Single Molecule Detection in Solution: Methods and Application," Chapter 3, Enderlein et al., Wiley-VCH, Germany, 2002.
Agrawal et al., "Counting single native biomolecules and intact viruses with color-coded nanoparticles" *Anal. Chem.*, 78:1061-1070, 2006.

(Continued)

*Primary Examiner* — Shafiqul Haq
(74) *Attorney, Agent, or Firm* — Parker Highlander PLLC

(57) ABSTRACT

A single molecule or molecule complex detection method is disclosed in certain aspects, comprising nano- or micro-fluidic channels.

10 Claims, 21 Drawing Sheets

(56) References Cited

OTHER PUBLICATIONS

Auroux et al., "Micro total analysis systems. 2. Analytical standard operations and applications," *Anal. Chem.*, 74:2637-2652, 2002.
Castro and Williams, "Single-molecule detection of specific nucleic acid sequences in unamplified genomic DNA" *Anal. Chem.*, 69:3915-3920, 1997.
Chan et al., "DNA mapping using microfluidic stretching and single-molecule detection of fluorescent site-specific tags," *Genome Research*, 14:1137-1146, 2004.
Chou et al., "A microfabricated device for sizing and sorting DNA molecules," *Proc. Natl. Acad. Sci. U.S.A.*, 96:11-13, 1999.
Craighead, "Future lab-on-a-chip technologies for interrogating individual molecules," *Nature*, 422:387-393, 2006.
De Mello, "Seeing single molecules," *Lab Chip*, 3:29N-34N, 2003.
Dittrich and Manz, "Single-molecule fluorescence detection in microfluidic channels—the Holy Grail in muTAS?," *Anal. Bioanal. Chem.*, 382:1771-1782, 2005.
Doherty et al., "Microchannel wall coatings for protein separations by capillary and chip electrophoresis" *Electrophresis*, 24:34-53, 2003.
Elf et al., "Probing transcription factor dynamics at the single-molecule level in a living cell" *Science*, 316:1191-1194, 2007.
Erim et al., "Performance of a Physically Adsorbed High-Molecular-Mass Polyethyleneimine Layer as Coating for the Separation of Basic Proteins and Peptides by Capillary Electrophoresis" *Journal of Chromatography A*, 708:356-361, 1995.
Foquet et al., "DNA fragment sizing by single molecule detection in submicrometer-sized closed fluidic channels," *Anal. Chem.*, 74:1415-1422, 2002.
Goodwin et al., "Single-molecule spectroscopy for nucleic acid analysis: a new approach for disease detection and genomic analysis" *Current Pharmaceutical Biotechnology*, 5:271, 2004.
Gosch et al., "Hydrodynamic flow profiling in microchannel structures by single molecule fluorescence correlation spectroscopy," *Anal. Chem.*, 72:3260-3265, 2000.
Haab and Mathies, "Single-molecule detection of DNA separations in microfabricated capillary electrophoresis chips employing focused molecular streams," *Anal. Chem.*, 71:5137-5145, 1999.
Haitao et al., "Molecule by molecule direct and quantitative counting of antibody-protein complexes in solution" *Anal. Chem.*, 76:4446-4451, 2004.
Haitao et al., "Ultrasensitive coincidence fluorescence detection of single DNA molecules" *Anal. Chem.*, 75:1664-1670, 2003.
Han and Craighead, "Entropic trapping and sieving of long DNA molecules in a nanofluidic channel," *J. Vac. Sci. Technol. A.*, 17(4):2142, 1999.
Han and Craighead, "Separation of long DNA molecules in a microfabricated entropic trap array," *Science*, 288:1026-1029, 2000.
Kim et al., "Real-time observation of temperature-dependent protein-protein interactions using real-time dual-color detection system." *Analytica Chimica Acta*, 577:163-170, 2006.
Knemeyer et al., "Probes for detection of specific DNA sequences at the single-molecule level," *Anal. Chem.*, 72(16):3717-3724, 2000.
Larson et al., "Single DNA molecule stretching in sudden mixed shear and elongational microflows," *Lab Chip*, 6:1187-1199, 2006.
Li et al., "In situ single-molecule detection of antibody-antigen binding by tapping-mode atomic force microscopy" *Anal. Chem.*, 74:6017-6022, 2002.
Mannion and Craighead, "Nanofluidic structures for single biomolecule fluorescent detection," *Biopolymer*, 85(2):131-143, 2007.
Mannion et al., "Conformational analysis of single DNA molecules undergoing entropically induced motion in nanochannels," *Biophysical Journal*, 90:4538-4545, 2006.
Michalet et al., "Quantum dots for live cells, in vivo imaging, and diagnostics" *Science*, 307:539-544, 2005.
PCT International Preliminary Report on Patentability, issued in International Application No. PCT/US2009/033577, mailing date Aug. 19, 2010.
PCT International Search Report and Written Opinion, issued in International Application No. PCT/US2009/033577, mailing date Sep. 10, 2009.
Pramanik, "Ligand-receptor interactions in live cells by fluorescence correlation spectroscopy" *Current Pharmaceutical Biotechnology*, 5:205-212, 2004.
Reyes et al., "Micro total analysis systems. 1. Introduction, theory, and technology," *Anal. Chem.*, 74:2623-2636, 2002.
Riehn et al., "Restriction mapping in nanofluidic devices," *Proc. Natl. Acad. Sci. U.S.A.*, 102:10012-10016, 2005.
Squires and Quake, "Microfluidics: fluid physics on the nanoliter scale," *Reviews of Modern Physics*, 77:977-1026, 2005.
Stavis et al., "Detection and identification of nucleic acid engineered fluorescent labels in submicrometer fluidic channels," *Nanotechnology*, 16:S314-S323, 2005.
Stavis et al., "Single molecule studies of quantum dot conjugates in a submicrometer fluidic channel," *Lab Chip*, 5(3):337-343, 2005.
Stone et al., "Engineering flows in small devices: Microfluidics toward a lab-on-a-chip," *Annu. Rev. Fluid. Mech.*, 36:381-411, 2004.
Tegenfeldt et al., "Micro- and nanofluidics for DNA analysis," *Anal. Bioanal. Chem.*, 378:1678-1692, 2004.
Turner et al., "Confinement-induced entropic recoil of single DNA molecules in a nanofluidic structure," *Phys. Rev. Lett.*, 88:128103, 2002.
Turner et al., "Monolithic nanofluid sieving structures for DNA manipulation" *J. Vac. Sci. Technol. B.*, 16(6):3835, 1998.
Van Orden et al., "Single-Molecule Identification in Flowing Sample Streams by Fluorescence Burst Size and Intraburst Fluorescence Decay Rate," *Anal. Chem.*, 70:1444-1451, 1998.
Vilkner et al., "Micro total analysis systems. Recent developments," *Anal. Chem.*, 76:3373-3386, 2004.
Visser et al., "Towards sorting of biolibraries using single-molecule fluorescence detection techniques" *Current Pharmaceutical Biotechnology*, 5:173-179, 2004.
Weiss, "Fluorescence spectroscopy of single biomolecules," *Science*, 283:1676-1683, 1999.
Weiss, "Measuring conformational dynamics of biomolecules by single molecule fluorescence spectroscopy," *Nature Structural Biology*, 7(9):724-729, 2000.
Widengren et al., "Single-molecule detection and identification of multiple species by multiparameter fluorescence detection." *Anal. Chem.*, 78:2039-2050, 2006.
Zhang and Johnson, "Homogenous rapid detection of nucleic acids using two-color quantum dots" *Analyst*, 131:484-488, 2006.

\* cited by examiner

| Cross Section View | Top View | Process |
|---|---|---|
| | | Double-side polished 4" fused silica wafer |
| | | Spin coat photoresist on wafer |
| | | Photolithography pattern the photoresist and develop |
| | | RIE etching fused silica substrate to desired depth |
| | | Removal of remaining photoresist |
| | | Creating fluid access holes |
| | | Fusion bonding of cover wafer to substrate wafer |

METHODS FOR DETECTING MOLECULE-MOLECULE INTERACTIONS WITH A SINGLE DETECTION CHANNEL

The present application is a national phase application under 35 U.S.C. §371 of International Patent Application PCT Application No. PCT/US2009/033577, filed Feb. 9, 2009, which claims the benefit of U.S. Provisional Application No. 61/026,978 filed Feb. 7, 2008. The entire contents of these applications are incorporated by reference.

BACKGROUND OF THE INVENTION

I. Field of the Invention

Embodiments of this invention are directed generally to biology, medicine, and diagnostics. In particular aspects of the invention are directed to detection of single molecule detection using two-dimensional photon counting analysis.

II. Background

Single molecule detection (SMD) with the assistance of micro/nano-fluidic devices has attracted tremendous amount of attention [1]. It provides a powerful way of biomolecular detection compare with conventional biosensors. Most conventional bio-analytical sensors utilize ensemble measurements and only yield information on the average for the entire population in a certain time frame. However, they seldom deal with heterogeneous samples, therefore, any fluctuation, reaction intermediate states, and time trajectories will affect the accuracy of detection in the conventional ensemble measurements [2]. SMD techniques, on the other hand, are able to provide us with invaluable information of molecular dynamics in many aspects that would otherwise be hidden and sometimes impossible to obtain with conventional techniques [3]. Micro/nano-fluidic technology has also developed rapidly over the last ten years [4-9]. It offers a spatial confinement of molecules in one or two dimensions in a continuous flow system. This will not only ensure a fixed position for interrogation of target molecules but also avoid repeated detection of the same molecule. As channel dimensions shrink and become comparable or smaller than the optical excitation volume, uniform excitation of target molecules and very high detection efficiency can be achieved. In addition, signal-to-noise ratio is improved significantly as the background from scattering and/or intrinsic fluorescence of unlabelled species in the probe volume is minimized. Sometimes SMD can be difficult to achieve while trying to investigate molecules in their native environment or at their physiological concentrations. With the help of micro/nano-fluidic devices, this has become feasible. The implementation of miniaturized devices greatly reduces sample consumption and as lab-on-a-chip technology advances, integrated high-throughput parallel detection system becomes feasible in the near future. By merging these two techniques, it is obvious that the inventors can achieve the optimal requirements for the analysis and manipulation of samples on a single molecule level [1, 10-12] and it had already found applications in many different fields, such as DNA separation [13-15], sequencing [16], mapping and fragment sizing [17-22], molecular conformation studies [23, 24], drug screening, chemical analysis [25,26], microflow characterization [27], and ultra-sensitive detection without target amplification [28].

Besides the aforementioned fields, molecule-molecule interaction studies at single molecule level in bulk solutions, on planer surfaces [29-35], and in microfluidic flowing environment [36-40] have become an active research area in recent years. Stavis and co-workers demonstrated efficient multicolor fluorescence detection and characterization of QD655 Streptavidin Conjugates binding to Alexa Fluor 488 molecules in a submicrometer fluidic channel [36]. Zhang et al. introduced a homogenous technique for rapid and sensitive probing specific DNA molecules using two-color quantum dots based on single-molecule coincidence detection in a capillary with inner diameter of 50 µm [40]. Most recently, Agrawal and co-workers reported the use of bioconjugated nanoparticles and two-color fluorescence coincidence for real-time detection of purified single gene, protein and intact virus in a flowing fused silica capillary with inner diameter of 2 µm [38]. Two-color channel detection is one of the common schemes in fluorescence-based molecule-molecule interaction studies at single molecule level. This requires two separated optical paths and detectors in the system. Spectral crosstalk still poses potential problems for two-color schemes but the use of quantum dots (QDs) with narrow emission bandwidth can alleviate the problem. However, very few specific protein detection studies are available currently in the literature due to difficulties in handling protein molecules in a fused silica microfluidic channel. There remains a need for additional methods for single molecule detection.

SUMMARY OF THE INVENTION

Certain embodiments are directed to a quick and sensitive method to detect rare molecules or molecule interactions is disclosed. Existing methods need more than two color dyes and two detection systems to detect multiple molecule interactions. In certain aspects the methods include an approach with polyclonal antibodies, a nanochannel, and a newly developed 2D photon counting diagram. These methods may need only one color dye and one detection system to identify molecular interactions. In addition, the approach may detect 2, 3, 4, 5, 6, 7, 8, up to 9 molecule interactions.

In certain aspects, the present invention includes, but is not limited to a detection scheme utilizing one fluorescent label to identify a protein (e.g., an enzyme, a transcription factor, a structural protein, and/or a signal transducing protein) from a sample in a surface-treated fused silica nanochannel. Continuous individual burst events are analyzed in terms of their photon counts and burst width. Based on their photon counts and burst width characteristics, the specific protein can be identified and distinguishable from non-target bound fluorescence signal. Assays and methods described herein offer simple, fast, and reliable alterative to conventional detection techniques. The use of only one color also reduces the complexity and cost of detection system as opposed to a two-color system. In still further aspects of the invention, a quantum dot can be used as fluorescence tag due to superb brightness, photochemical stability, and quantum yield over traditional organic dyes [41].

In some embodiments, features of the approach include a polyclonal antibody, a 2D photon diagram, and a nanochannel. Use of the features may realize the detection of multiple molecule interactions with only one fluorescent dye and one detection channel.

Detection of molecule-molecule interaction typically requires more than two fluorescent dye molecules with two optical detection systems (beam splitter, optical fiber and avalanche photo diode), and their cross correlation curve is utilized to identify the molecule binding status. In aspects of this method, the binding status is averaged over the time. In certain embodiments, the method includes one detection system and reduces the cost of the detection of multiple molecular interactions.

Multiple molecule-molecule interactions with two detection systems are disclosed in U.S. Pat. Nos. 6,355,420; 6,927,065; and 6,762,065, which are incorporated by reference herein in their entirety.

Certain aspects include methods comprising: (a) contacting a sample with a binding moiety that specifically binds to a target molecule of the sample; (b) contacting the binding moiety with a detection moiety forming a detection complex; (c) introducing the sample containing the detection complex into a channel of at least 100 nm in width; and (d) detecting the complex by 2D photon counting. In a further aspect the method can further comprise contacting the sample with a second binding moiety and a second detection moiety; or a third binding moiety and a third detection moiety.

In certain embodiments the binding moiety is an antibody, such as a polyclonal antibody.

In a further aspect, the detection moiety is an antibody that specifically binds the binding moiety. The detection moiety can comprise a fluorophore. The fluorophore can be a quantum dot or a fluorescent dye.

In certain embodiments the nanochannel is coated with a positively charged polymer, such as polyethylenimine (PEI).

In still other embodiments a sample is a tissue or cell lysate. In certain aspects the sample contains a target molecule, such as a protein or a protein complex, or a nucleic acid.

In a further embodiment, the channel is at least 0.25, 0.5, 0.75, 1, 1.5, 2, 2.5, 3.0 µm in width, including all values and ranges there between.

A "ligand" or "target molecule" generally refers to any molecule that binds to an anti-ligand or binding moiety to form a ligand/antiligand pair or a target complex. Thus, a ligand is any molecule for which there exists another molecule (e.g., the antiligand or target binding moiety) that specifically or non-specifically binds to the ligand, owing to recognition of some portion or feature of the ligand.

An "antiligand" or "binding moiety" is a molecule that specifically or nonspecifically interacts with another molecule (e.g, the ligand or target molecule).

As used herein, the term "binding pair" or "binding partners" refers to first and second molecules that specifically bind to each other such as a ligand and an antiligand. In general, "specific binding" of the first member of the binding pair to the second member of the binding pair in a sample is evidenced by the binding of the first member to the second member, or vice versa, with greater affinity and specificity than to other components in the sample. The binding between the members of the binding pair is typically noncovalent. Binding partners need not be limited to pairs of single molecules. For example, a single ligand can be bound by the coordinated action of two or more antiligands. Binding between binding pairs or binding partners results in the formation of a binding complex, sometimes referred to as a ligand/antiligand complex or simply as ligand/antiligand. Exemplary binding pairs include, but are not limited to: (a) a haptenic or antigenic compound in combination with a corresponding antibody or binding portion or fragment thereof, (b) nonimmunological binding pairs (e.g., biotin-avidin, biotin-streptavidin, biotin-Neutravidin); (c) hormone-hormone binding protein; (d) receptor-receptor agonist or antagonist; (e) lectin-carbohydrate; (f) enzyme-enzyme cofactor; (g) enzyme-enzyme inhibitor; (h) and complementary polynucleotide pairs capable of forming nucleic acid duplexes.

An "analyte" or "target" refers to the species whose presence, absence and/or concentration is being detected or assayed.

"Polypeptide," "peptides" and "protein" are used interchangeably herein and include a molecular chain of amino acids linked through peptide bonds. The terms do not refer to a specific length of the product. The terms include post-translational modifications of the polypeptide, for example, glycosylations, acetylations, phosphorylations and the like, and also can include polypeptides that include amino acid analogs and modified peptide backbones.

The term "antibody" as used herein includes antibodies obtained from both polyclonal and monoclonal preparations, as well as the following: (i) hybrid (chimeric) antibody molecules (see, for example, Winter et al. (1991) Nature 349:293-299; and U.S. Pat. No. 4,816,567); (ii) F(ab')$_2$ and F(ab) fragments; (iii) Fv molecules (noncovalent heterodimers, see, for example, Inbar et al. (1972) Proc. Natl. Acad. Sci. USA 69:2659-2662; and Ehrlich et al. (1980) Biochem 19:4091-4096); (iv) single-chain Fv molecules (sFv) (see, for example, Huston et al. (1988) Proc. Natl. Acad. Sci. USA 85:5879-5883); (v) dimeric and trimeric antibody fragment constructs; (vi) humanized antibody molecules (see, for example, Riechmann et al. (1988) Nature 332:323-327; Verhoeyan et al. (1988) Science 239: 1534-1536; and U. K. Patent Publication No. GB 2,276,169, published 21 Sep. 1994); (vii) Mini-antibodies or minibodies (i.e., sFv polypeptide chains that include oligomerization domains at their C-termini, separated from the sFv by a hinge region; see, e.g., Pack et al. (1992) Biochem 31:1579-1584; Cumber et al. (1992) J. Immunology 149B:120-126); and, (vii) any functional fragments obtained from such molecules, wherein such fragments retain specific-binding properties of the parent antibody molecule.

The phrase "specifically binds" generally refers to binding of a ligand and an antiligand, or vice versa, with greater affinity and specificity than to other components in the sample. Thus, the term refers to a binding reaction which is determinative of the presence of the ligand in the presence of a heterogeneous population of other biological compounds. Thus, under designated conditions, a specified ligand binds preferentially to a particular antiligand and does not bind in a significant amount to other molecules present in the sample. Typically, a molecule or ligand (e.g., an antibody) that specifically binds to an antiligand has an association constant of at least $10^3$ M$^{-1}$ or $10^4$ M$^{-1}$, sometimes $10^5$ M$^{-1}$ or $10^6$ M$^{-1}$, in other instances $10^6$ M$^{-1}$ or $10^7$ M$^{-1}$, preferably $10^8$ M$^{-1}$ to $10^9$ M$^{-1}$, and more preferably, about $10^{10}$ M$^{-1}$ to $10^{11}$ M$^{-1}$ or higher.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1A:
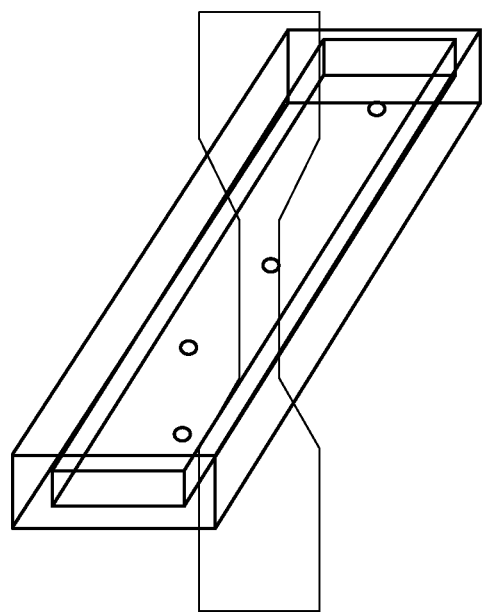
FIG. 1. Optics and channel diagram. (A) Diagram of single molecular detection in the channel. The fluorescence signal will be stimulated by laser and detected by FCS. (B) SEM image of the channel.

Certain embodiments include a microfluidic based single molecule detection method. In certain aspects the single molecule detection methods uses flow proteometry for detecting a specific protein in a sample, e.g., lysed mammalian cell or sample obtained from a subject. In a further aspect methods of the invention employ surface modification protocols to reduce protein adsorption to fused silica. These surface modification protocols significantly improve detection efficiency. Unlike the conventional immuno-detections, the relatively high sensitivity and selectivity of this technique allow the use of very small amounts of sample with no purification steps required for detection. Analysis time is reduced tremendously with this assay as well.

The concept of two-dimensional plot for data analysis is also introduced herein. Each individual event is located on the 2D plot based on its photon counts and burst width. The coordinates of individual event on 2D plot serves as a molecular fingerprint of mass-to-charge ratio for different fluorescent molecules or complex as they are electrokinetically driven through the excitation volume. Thus, the detection scheme described together with the 2D plot analysis offers considerable advantages over current bio-analytical techniques in identifying specific target proteins.

Among conventional bioanalytical techniques, immunoassays are commonly used to detect specific protein and assess protein-protein interaction present in cell extracts. Taking advantage of miniaturized devices, the techniques described offer a simple, fast and accurate immunoassay, which only needs a small amount of sample. However, without surface treatment, surface adsorption of proteins is observed in fused silica nanofluidic channel. Surface modification using positively charged polymer, such as polyethylenimine (PEI) significantly increases the signal at the detection region (sufficient molecules may be detected for analysis during the reasonable time span). In addition, sample concentration used in these methods is at least two orders of magnitude lower than concentration where on average only one molecule is calculated to be in the focal volume at one time. This ensures the single molecule resolution for data analysis to be valid. Similar to conventional immunoassay, the interaction between antibody and antigen and the ability of antibody recognizing specific antigen is exploited. Polyclonal antibodies are able to recognize a variety of epitopes on a single antigen. In certain aspects, polyclonal primary antibody (e.g., rabbit anti-HA) may be used and it is expected that multiple primary antibodies will bind to one detection target in a sample. A fluorescent tag or label (e.g., QD525) can be bound to the primary antibody through a secondary antibody. There is relatively high probability that one protein complex is associated with multiple labels (e.g., QD525s) based on the relative concentrations for each specie. Therefore, from 2D plot target protein/label complex in the mixture of un-bound or target bound labels can be distinguished based on the fluorescent photon counts for each individual event.

I. MICRO- OR NANO-FLUIDICS

A submicrometer fluid channel, also referred to as a nanofluidic channel or microfluidic channel, is a nanofabricated structure that physically constrains the sample in two dimensions, one lateral and one axial, reducing the number of unwanted fluorophores detected. Another property of the nanofluidic channels is the ability to flow single molecules through the detection volume with a high degree of control. This enables a balance of several factors important to single molecule detection and analysis, including detection efficiency and rates of throughput and data acquisition. While the nanofluidic channel has been described as a channel having a cross section of approximately 500 nm square, other sizes of channels having similar characteristics may be used.

A detection complex or a conjugate may be driven through the channel electrokinetically at 10, 25, 50, 75, 100, 125, 150, or 200 V/cm (including all values and ranges there between) excited with a laser, and detected with a confocal microscope. In certain aspects, signal rejection can be minimized by the narrow and symmetric emission spectra of quantum dots. Other means may also be used to drive the conjugates through the nanochannels, such as pressure based devices, centrifugal force, hydrostatic, and gravity based drivers. A number of nano-fluidic devices can be used to perform the methods describe herein.

II. DETECTION MOIETY/COMPLEX

A. Binding Moiety

In certain aspects, a binding moiety binds to a target molecule with specificity. Target molecules that can be detected by the method of the invention include antigenic analytes, such as proteins, the binding moiety then suitably being immunological binding partners. The immunological binding partners that can be used in the invention include polyclonal antibodies of any species (including chimeric antibodies and/or recombinant antibodies) or fragments thereof, for example, Fab, Fab' or F(ab')$_2$ fragments. Monoclonal antibodies or fragments thereof can also be used because of their capacity of being produced identically in unlimited amounts.

B. Signal Moiety

A detection moiety of the invention will be capable of binding a target molecule and either directly or indirectly emitting a detectable signal. In certain aspects a binding moiety will be bound to a target molecule. The binding moiety will then be bound or coupled to a signaling or detection moiety. The detection moiety is bound or is coupled to a label that can be detected using the methods described herein. In another aspect, the label can be directly coupled to the binding moiety.

Label selection plays an important role in single molecule studies. Ionic dyes, the standard choice in fluorescence microscopy assays, have several advantageous properties that make them well suited to single molecule studies. These include fluorescence quantum efficiencies approaching unity and fluorescence lifetimes below 10 ns. Accordingly, xanthene dyes such as Rhodamine 6G and tetremethylrhodamine isothyiocyanate are commonly used in single molecule studies. It is also becoming increasingly popular to use naturally occurring fluorescent proteins in single molecule studies. For example, Green Fluorescent Protein is resistant to photobleaching because its chromophore is located within the interior of its "β-can" structure and is thus protected from molecular oxygen. Almost all of these organic dyes exhibit broad emission spectra. These broad emission spectra make multi-fluorophore single molecule studies virtually impossible. An alternative to organic dyes is semiconductor nanoparticles or quantum dots.

Label selection is guided primarily by the necessity of having a signal to noise ratio large enough that single molecules can be detected and analyzed. Because of their high extinction coefficients and quantum yields, quantum dots are exceptionally bright, making them valuable for single molecule studies. Quantum dots are also highly photostable. In a multicolor experiment there are considerations beyond the basic ability to detect single molecules, such as the spectral properties of the fluorescent labels. In order to isolate fluorescence emission from a single species of fluorophore, the Stokes shift must be large enough to resolve the emission and excitation peaks. In a multicolor experiment, this situation can be complicated by multiple fluorescent species with overlapping emission and excitation spectra. Typically, when standard organic fluorophores are used, overlap in the emission spectra is managed by restricting the spectral range of collected fluorescence. This results in rejected signal and reduced detection efficiency.

The term "label" refers to a molecule or an aspect of a molecule that can be detected by physical, chemical, electromagnetic and other related analytical techniques. Examples of detectable labels that can be utilized include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates. The term "detectably labeled" means that an agent has been conjugated with a label or that an agent has some inherent characteristic (e.g., size, shape or color) that allows it to be detected without having to be conjugated to a separate label.

Suitable labels or dyes or fluorophores include, without limitation, fluorescent dyes such as d-Rhodamine dye including dichloro[R110], dichloro[R6G], dichloro[TAMRA], dichloro[ROX] or the like, fluorescein dye including fluorescein, 6-FAM, or the like; Acridine including Acridine orange, Acridine yellow, Proflavin, or the like; Aromatic Hydrocarbon including 2-Methylbenzoxazole, Ethyl p-dimethylaminobenzoate, Phenol, Pyrrole, benzene, toluene, or the like; Arylmethine Dyes including Auramine O, Crystal violet, Crystal violet, Malachite Green or the like; Coumarin dyes including 7-Methoxycoumarin-4-acetic acid, Coumarin 1, Coumarin 30, Coumarin 314, Coumarin 343, Coumarin 6 or the like; Cyanine Dye including 1,1'-diethyl-2,2'-cyanine iodide, Cryptocyanine, Indocarbocyanine (C3) dye, Indodicarbocyanine (C5) dye, Indotricarbocyanine (C7) dye, Oxacarbocyanine (C3) dye, Oxadicarbocyanine (C5) dye, Oxatricarbocyanine (C7) dye, Pinacyanol iodide, Stains all, Thiacarbocyanine (C3) dye, Thiacarbocyanine (C3) dye, Thiadicarbocyanine (C5) dye, Thiatricarbocyanine (C7) dye, or the like; Dipyrrin dyes including N,N'-Difluoroboryl-1,9-dimethyl-5-(4-iodophenyl)-dipyrrin, N,N'-Difluoroboryl-1, 9-dimethyl-5-[(4-(2-trimethylsilylethynyl), N,N'-Difluoroboryl-1,9-dimethyl-5-phenydipyrrin, or the like; Merocyanines including 4-(dicyanomethylene)-2-methyl-6-(p-dimethylaminostyryl)-4H-pyran (DCM), acetonitrile, 4-(dicyanomethylene)-2-methyl-6-(p-dimethylaminostyryl)-4H-pyran (DCM), 4-Dimethylamino-4'-nitrostilbene, Merocyanine 540, or the like; Miscellaneous Dye including 4',6-Diamidino-2-phenylindole (DAPI), 4',6-Diamidino-2-phenylindole (DAPI), 7-Benzylamino-4-nitrobenz-2-oxa-1,3-diazole, Dansyl glycine, Dansyl glycine, Hoechst 33258, Hoechst 33258, Lucifer yellow CH, Piroxicam, Quinine sulfate, Quinine sulfate, Squarylium dye III, or the like; Oligophenylenes including 2,5-Diphenyloxazole (PPO), Biphenyl, POPOP, p-Quaterphenyl, p-Terphenyl, or the like; Oxazines including Cresyl violet perchlorate, Nile Blue, Nile Red, Nile blue, Oxazine 1, Oxazine 170, or the like; Polycyclic Aromatic Hydrocarbons including 9,10-Bis (phenylethynyl)anthracene, 9,10-Diphenylanthracene, Anthracene, Naphthalene, Perylene, Pyrene, or the like; polyene/polyynes including 1,2-diphenylacetylene, 1,4-diphenylbutadiene, 1,4-diphenylbutadiyne, 1,6-Diphenylhexatriene, Beta-carotene, Stilbene, or the like; Redox-active Chromophores including Anthraquinone, Azobenzene, Benzoquinone, Ferrocene, Riboflavin, Tris(2,2'-bipyridyl)ruthenium(II), Tetrapyrrole, Bilirubin, Chlorophyll a, Chlorophyll a, Chlorophyll b, Diprotonated-tetraphenylporphyrin, Hematin, Magnesium octaethylporphyrin, Magnesium octaethylporphyrin (MgOEP), Magnesium phthalocyanine (MgPc), Magnesium phthalocyanine (MgPc), Magnesium tetramesitylporphyrin (MgTMP), Magnesium tetraphenylporphyrin (MgTPP), Octaethylporphyrin, Phthalocyanine (Pc), Porphin, Tetra-t-butylazaporphine, Tetra-t-butylnaphthalocyanine, Tetrakis(2,6-dichlorophenyl)porphyrin, Tetrakis(o-aminophenyl)porphyrin, Tetramesitylporphyrin (TMP), Tetraphenylporphyrin (TPP), Vitamin B12, Zinc octaethylporphyrin (ZnOEP), Zinc phthalocyanine (ZnPc), Zinc tetramesitylporphyrin (ZnTMP), Zinc tetramesitylporphyrin radical cation, Zinc tetraphenylporphyrin (ZnTPP), or the like; Xanthenes including Eosin Y, Fluorescein, Fluorescein, Rhodamine 123, Rhodamine 6G, Rhodamine B, Rose bengal, Sulforhodamine 101, or the like; or mixtures or combination thereof or synthetic derivatives thereof or FRET fluorophore-quencher pairs including DLO-FB1 (5'-FAM/3'-BHQ-1) DLO-TEB1 (5'-TET/3'-BHQ-1), DLO-JB 1 (5'-JOE/3'-BHQ-1), DLO-HB 1 (5'-HEX/3'-BHQ-1), DL0-C3B Cy3/3'-BHQ-2), DLO-TAB2 (5'-TAMRA/3'-BHQ-2), DLO-RB2 (5'-ROX/3'-BHQ-2), DL0-C5B3 (5'-Cy5/3'-BHQ-3), DL0-C55B3 (5'-Cy5.5/3'-BHQ-3), MBO-FB1 (5'-FAM/3'-BHQ-1), MBO-TEB1 (5'-TET/3'-BHQ-1), MBO-JB1 (5'-JOE/3'-BHQ-1), MBO-HB1 (5'-HEX/3'-BHQ-1), MBO-C3B2 (5'-Cy3/3'-BHQ-2), MBO-TAB2 (5'-TAMRA/3'-BHQ-2), MBO-RB2 (5'-ROX/3'-BHQ-2); MBO-C5B3 (5'-Cy5/3'-BHQ-3), MBO-C55B3 (5'-Cy5.5/3'-BHQ-3) or similar FRET pairs available from Biosearch Technologies, Inc. of Novato, Calif. or any other fluorescent donor or acceptor.

Compared to standard organic fluorophores, quantum dots have narrow and symmetrical emission spectra. Quantum dots also display a large effective Stokes shift, and different quantum dots can be excited by the same excitation source, typically in the blue part of the spectrum. The union of these traits results in the ability to simultaneously excite several species of quantum dots, or combinations of quantum dots and organic fluorophores, with a single light source, while the emission spectra are easily and entirely resolved. This increased detection efficiency is particularly relevant in single molecule detections where signal to noise ratio is often a limiting factor.

Quantum dot is a preferred example. Quantum dots are nanometer scale particles that absorb light, then quickly re-emit the light but in a different wavelength and thus color. The dots have optical properties that can be readily customized by changing the size or composition of the dots. Quantum dots are available in multiple colors and brightness, offered by either fluorescent dyes or semiconductor LEDs (light emitting diodes). In addition, quantum dot particles have many unique optical properties such as the ability to tune the absorption and emission wavelength by changing the size of the dot. Thus different-sized quantum dots emit light of different wavelengths. Quantum dots have been described in U.S. Pat. No. 6,207,392, and are commercially available from Quantum Dot Corporation. Quantum dots are defined in more detail in U.S. Patent Publication 20070166743, which is incorporated herein by reference in its entirety.

Quantum dots are composed of a core and a shell. The core is generally composed of cadmium selenide (CdSe), cadmium telluride (CdTe), or indium arsenide (InAs). CdSe provides emission on the visible range, CdTe in the red near infrared, and InAs in the near infrared (NIR). The composition and the size of the spherical core determine the optical properties of the quantum dot. For instance, a 3 nm CdSe quantum dot produces a 520 nm emission, a 5.5 nm CdSe quantum dot produces a 630 nm emission, and intermediate sizes result in intermediate colors. The emission width is controlled by the size distribution.

For example, Quantum Dot 525 (QD525) conjugated goat anti rabbit antibody (Invitrogen) was used to characterize the detection of QD525 in the microchannel. QD525 conjugated antibody (1 µM) was diluted in Immuno-precipitation buffer (IP buffer, 20 mM Hepes-KOH, 0.1 mM KCl, 2 mM $MgCl_2$, 15 mM NaCl, 0.2 mM EDTA, 1 mM DTT, 10% glycerol) in 1:5000 ratio. The sample was then loaded into the microchannel for single fluorescence signal detection. For specific protein detection, Hemagglutinin (HA) epitope tagged MAX cDNA was transfected and overexpressed in HEK293 cell line. The cells were then lysed by RIPA lysis buffer and total cell lysates were collected to measure the protein concentration before subsequent analysis. 500 µg of protein lysate sample was diluted in IP binding buffer and made it to final total 1 ml. 500 µg of rabbit anti-HA tag primarily polyclonal antibody (Santa cruz, 200 mg/ml) was then added into the sample and rotated in 4° C. for overnight. Subsequently, 2 µl of QD525 conjugated anti-rabbit antibody (1 µM) was added into the sample and incubated in room temperature for 1 hour and then diluted 10 times in IP binding buffer. The sample was then loaded into the nanochannel for the single molecular detection.

Quantum dots tend to be highly photostable, with fluorescence decay lifetimes ranging from nanoseconds to microseconds. Hence, these particles are ideal for single molecule spectroscopy due to their improved spectral properties when compared to typical organic dyes. Quantum dots such as CdSe also tend to have a much narrower full width at half maximum and much more symmetrical emission spectra when compared to their organic counterparts. There is no overlap between both spectra, making a two color single molecule study error free in the sense that there is no cross talk between the red and green channels. If standard organic fluorophores were used, this would not be possible, as overlap in emission spectra would directly result in a false positive signal in a given detection channel. When organic fluorophores are used in a multicolor experiment the collected photons are typically restricted to a specific region of the emission spectra in order to ensure no cross talk between channels. This results in lower overall signal intensities and detection efficiency. On the other hand, the entire emission spectrum of quantum dots is utilized as the spectral full width at half maximum can be as low as 40 nm.

Quantum dots have diverse applications, and have recently been studied in a variety of fluorescence microscopy and biological assays. Single quantum dots have been detected using a variety of microscope configurations, including with a diffraction-limited spot, with near-field scanning optical microscopy and on a substrate using total internal reflection microscopy. Quantum dots have also been used as fluorescent labels in live cells and for in vivo multiphoton microscopy. Because of their unique and beneficial optical properties, quantum dots have potential as fluorescent labels in single molecule studies.

III. DETECTION METHODS

Certain aspects of the present invention contains a detection method comprising two dimensional (2D) photon counting. Traditional FCS analysis only yields an average information for a particular measurement of collective individual molecules [44-45]. If the sample is heterogeneous, valuable information of individual molecule could be masked by the average. This is usually the case when studying molecule-molecule interaction since bound/unbound ratio could vary significantly under different circumstances. Two-color cross-correlation was then developed at this point to improve the accuracy [44]. However, two-color will inevitably increase the complexity of the system and present new challenges for detection, such as excitation efficiency of different fluorescent labels, spectrum overlapping of two fluorescent labels, etc. 2D photon counting is an alternative way to present the information of individual molecules. A collective of photon burst events in a certain time span are first analyzed individually and a two-dimensional (2D) plot of photon burst width versus photon counts for each burst event is generated. This provides characteristic information of different molecules depending on their spatial locations on the 2D plot.

For example, to get this 2D plot, a control study of a single quantum dot 525 (QD525) conjugated secondary antibody in microchannel was first performed at different applied voltages and their respective autocorrelations were obtained with the ISS Vista™ software. After fitting the autocorrelation with the built-in flow model, average flow velocities of QD525 in microchannel for different potentials is obtained. Since the focal volume radius is known, the average residence time of QD525 in the detection volume could be estimated. Thereafter, photon burst data are binned with a time, which was slightly longer than this residence time, to ensure single molecule resolution. After binning, the raw data (ASCII format) of photon burst signals is extracted and average intensity calculated with standard deviation ($\sigma$) for a particular measurement. It is assumed photon burst follows Poissonian Distribution [26], the $\sigma$ was calculated to be square root of average intensity. To identify the individual molecule, the photon burst threshold value is set to average+3*$\sigma$[1]. Intensity higher than the threshold was identified as signal while those below the threshold was considered as noise. Once the position of the signal is determined, the photon burst raw data can be re-binned with a different time, e.g., a time 10 times shorter than the previous bin time. In this newly-binned photon burst data, the previous identified signal was located and its photon burst width in time and total counts were obtained to generate a 2D plot. This process can be repeated for different burst signals and more than 100 data points for each condition recorded. The same data analysis procedure can be performed with protein detection data. The fluorescence photon burst experiment was performed on an Alba Fluorescence Correlation Spectrometer (FCS)™ system by ISS Inc. (Champaign, Ill.). This system is equipped a 370 nm diode laser with an average power of 20 µW at objective. The schematic configuration of the system is shown in the FIG. 2. To ensure a good signal-to-noise ratio, a 63× Nikon water immersion objective with numerical aperture of 1.2 was used. The effective detection region is 0.5 µm in diameter, which is defined by the confocal pin hole size of the system. Sample in microchannel is electrokinetically driven at various potentials. Fluorescence photon burst raw data is collected at a sampling frequency of 100 k for 50 seconds.

Certain methods utilize an optical microscope to examine the different detection sections in the different flow channels. The objective lens of the microscope is directed towards the detection section. Typically, a mercury arc lamp or argon laser is utilized as the light source. The microfluidic device can be mounted on a translation stage such that the various detection sections can be positioned by translation over the objective lens. Additional details regarding the use of microscopes with microfluidic devices similar to those described herein are provided in PCT publication WO 99/61888.

Detection methodologies that can be utilized in the screening process include, and are not limited to: (1) fluorescence intensity, (2) fluorescence polarization, (3) fluorescence resonance energy transfer (FRET), (4) heterogeneous time resolved fluorescence (HTRF) or time-resolved energy transfer (TRET), (5) Fluorescence correlation spectroscopy (FCS) and related techniques (such as fluorescence intensity distribution analysis (FIDA). (see, e.g., Pope et al. (1999) Drug Discovery Today 4: 350-362; Kask et al. (1999) Proc. Natl. Acad. Sci. USA. 96: 13756-61; Moore et al. (1999) J. Biomol. Screening 4: 335-353; and Auer et al. (1999) Drug Discovery Today 3: 457-465). A more detailed discussion of these detection options follows.

Fluorescence intensity: Measurement of the intensity of fluorescence of a sample provides a direct measurement of fluorophore concentration. This technique is often used in enzyme assays, where an enzyme activity is measured using a non-fluorescent substrate that is converted to a fluorescent product by the action of the enzyme (i.e., a fluorogenic substrate). Other assays that measure fluorescence directly include calcium binding assays, in which the fluorescence of the calcium binding dye is significantly increased upon binding calcium. Thus, the detector in certain systems is an instrument able to detect fluorescence intensity from the detection section of the microfluidic device.

Fluorescence polarization: Fluorescence polarization (FP) is another common detection technique that can be utilized with the microfluidic devices provided herein. The theory of FP is that when a fluorophore is excited with polarized light, the emitted light is also polarized. This occurs because excitation is dependent upon the orientation of the fluorophore dipole to the excitation beam. The emitted light is depolarized upon rotational diffusion of the fluorophore. For a small molecule fluorophore, this occurs rapidly and the emitted light is isotropic. Changes in the rotational diffusion time of a small fluorophore occur when it becomes bound to a much larger molecule and lead to measurable anisotropy in the emitted light. Thus, FP can be utilized in a wide variety of assays in which in certain circumstances a fluorescently labeled agent is part of a large molecule that tumbles relatively slowly, whereas in other circumstances the labeled agent is free in solution and able to tumble more rapidly. Examples of such assays include assays involving binding of a labeled ligand to a cell-surface receptor, ligand/antiligand binding (e.g., ligand/receptor binding) and a labeled protein substrate and a labeled cleavage product.

Fluorescence polarization is determined by measuring the vertical and horizontal components of fluorophore emission following excitation with plane polarized light. Light from a monochromatic source (at an appropriate excitation wavelength) passes through a vertical polarizing filter to excite fluorescent molecules in the sample. Only those molecules that are orientated in the vertically polarized plane absorb light, become excited, and subsequently emit light. The emission light intensity is measured both parallel and perpendicular to the exciting light. The fraction of the original incident, vertical light intensity that is emitted in the horizontal plane is a measure of the amount of rotation the fluorescently labeled molecule has undergone during the excited state, and therefore is a measure of its relative size. Thus, the detector used to monitor FP in the microfluidic device includes the elements necessary to make the foregoing measurements. A number of commercially-available FP instruments can be used in conjunction with the present microfluidic devices (e.g., systems from Panvera Corp). Additional guidance regarding FP detection is provided, for example, by Chen et al. (1999) Genome Research 9: 492-8; and in U.S. Pat. No. 5,593,867 to Walker et al.

Fluorescence resonance energy transfer (FRET): This technique is dependent upon non-radioactive transfer between two fluorophores (a donor and an acceptor) that occurs when they come into close proximity (<5 nm). The efficiency of transfer highly dependent upon the distance between the fluorophores, their physical properties and the spectral overlap between them. Under FRET conditions, excitation at the donor excitation maximum is efficiently transferred to the acceptor and emitted at the acceptor emission wavelength. This property can be exploited in many different types of assays that can either bring fluorophores together (increased FRET) or separate them (decreased FRET). Thus, FRET assays can be conducted by detecting an increase in the fluorescence intensity of the acceptor and a decrease in fluorescence intensity of the acceptor. Alternatively, changes in the ratio of emission at the donor emission maximum to emission at the acceptor maximum can be used to follow increases or decreases in FRET. The present microfluidic devices can be utilized in FRET assays in conjunction with commercially-available fluorescent readers. These systems include a source to activate the acceptor fluorophore and then detect alterations in the emissions from the donor and/or acceptor fluorophore.

A number of fluorophores suitable for conducting assays described herein are known. Specific examples include, 6-carboxy fluorescein (FAM), 5&6-carboxyrhodamine-110 (R110), 6-carboxyrhodamine-6G (R6G), N,N,N',N'-tetramethyl-6-carboxyrhodamine (TAMRA), 6-carboxy-X-rhodamine (ROX), 6-carboxy-4',5'-dichloro-2',7'-dimethoxyfluorescein (JOE), ALEXA Fluor™, Cy2, Texas Red and Rhodamine Red. Additional fluorescent dyes available from Applied Biosystems Division of Perkin Elmer Corporation (Foster City, Calif.) include, 6-carboxy-2',4,7,7'-tetrachlorofluorescein (TET), 6-carboxy-2',4,4',5',7,7'-hexachlorofluorescein (HEX), 5-carboxy-2',4',5',7'-tetrachlorofluorescein (ZOE), NAN, NED; fluorophores available from Amersham Pharmacia Biotech (Piscataway, N.J.) include, Cy3, Cy3.5, Cy5, Cy5.5, Cy7, and Cy7.5.

Further guidance regarding the selection of donor and acceptor pairs that can effectively be used in FRET-based assays include: Fluorescence Spectroscopy (Pesce et al., Eds.) Marcel Dekker, New York, (1971); White et al., Fluorescence Analysis: A Practical Approach, Marcel Dekker, New York, (1970); Berlman, Handbook of Fluorescence Spectra of Aromatic Molecules, 2nd ed., Academic Press, New York, (1971); Griffiths, Colour and Constitution of Organic Molecules, Academic Press, New York, (1976); Indicators (Bishop, Ed.). Pergamon Press, Oxford, 19723; and Haugland, Handbook of Fluorescent Probes and Research Chemicals, Molecular Probes, Eugene (1992).

Another option is to use various fluorescent proteins. Examples include green fluorescent protein (GFP), blue fluorescent protein (BFP), yellow fluorescent protein and ds Red (a red fluorescent protein).

Time-resolved techniques: A variety of time-resolved fluorescent techniques can be utilized. One such technique is heterogeneous time-resolved fluorescence (HTRF) or time resolved energy transfer (TRET). This method uses fluorescence resonance energy transfer between two fluorophores. The most commonly used donor is europium cryptate (EuK), which absorbs light at 337 nm and emits at 620 nm. Other commonly used long-lived donors are lanthanates ($Ln^{3+}$).

EuK can transmit this energy in a non-radioactive fashion to an appropriate acceptor, such as XL665 (a modified allophycocyanin) when the acceptor-donor pair are in close proximity (<5-10 nm). When excited at 620 nm, XL665 emits light with a slow decay at 665 nm. Detection is performed after a defined delay (usually about µs) as the measured ratio of fluorescence at 665 nm to fluorescence at 620 nm ($F_{665}/F_{620}$). The advantage of using an acceptor-donor pair with long lifetimes is that background fluorescence decays more rapidly than the desired signal, and consequently HTRF is extremely sensitive.

Fluorescence correlation spectroscopy (FCS): This method is based upon the recognition that as a fluorescently labeled molecule passes through a confocal laser beam and is excited, it emits photons of fluorescent light. The length of each photon burst is dependent upon the time spent in the confocal beam, and is diffusion controlled. By measuring the time associated with each burst, diffusion coefficients can be calculated, allowing discrimination of fluorescent molecules, such as bound and free species in a solution. Quantitation of free and bound ligand therefore allows determination of absolute concentrations of fluorophores and degree of binding. FCS is insensitive to miniaturization and therefore useful for implementation in microfluidic devices. When utilized with the present devices, a confocal laser is oriented such that the beam it emits is directed towards the detection section. The fluorescent detector is positioned to receive the photons of emitted light received from the detection section.

Ligands in Detection Section: Certain detection methods involve immobilizing an antiligand within the detection section. In this way, ligands that specifically bind to the antiligand can be captured and detected within the detection section. Often the antiligand is an immunological agent such as an antibody.

Single Molecule and Single Cell Measurements: Certain detection units that can be utilized with the systems described herein permit the detection and measurement of single molecules or cells. This capability can enable one to study processes that might not be apparent when making measurements of ensemble averages of populations of molecules or cells. In particular, such measurements allow observation of subpopulations of events within apparently homogeneous systems, and the analysis of dynamic events occurring on different time scales that would be lost upon averaging (see, e.g., Ishii, Y. and Yanagida, T. (2000) Single Mol. 1: 5-16 and Weiss S. (1999) Science 283: 676-1683. Fluorescence Correlation Spectroscopy (FCS; described supra) is one example of an intrinsically single molecule detection technique in which such detection units are useful. However, with standard optics, one can readily detect events at the single molecule or single cell level in essentially all of the modes described above (fluorescence intensity, fluorescence polarization, fluorescence resonance energy transfer (FRET), and fluorescence correlation spectroscopy (FCS)). Optical systems for the detection of single DNA molecules and cells in microfluidic devices are described in PCT Publication WO 99/61888, which is incorporated by reference in their entirety for all purposes.

IV. EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Figure 1B:
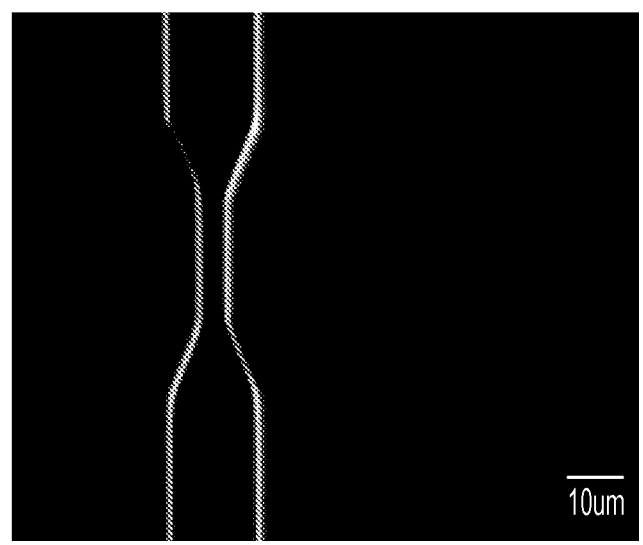
Figure 2A:
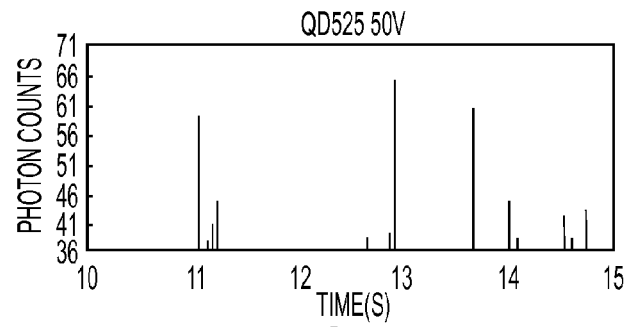
FIG. 2. Photon Burst of QD525 conjugated antibody in the channel (A-C) Different application voltages lead to various frequency of events occur and the voltage dependent will flow rate also affected the photon burst intensity. (D) Amplified and normalized data of selected region in (B).
Figure 2B:
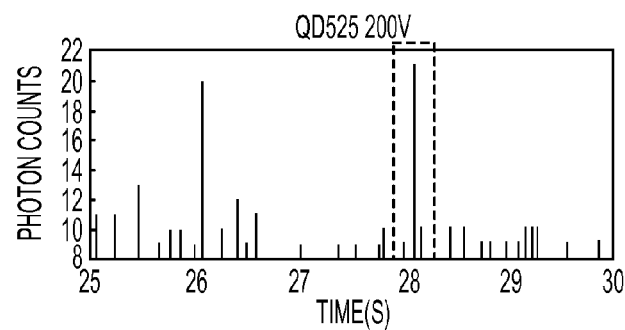
Figure 2C:
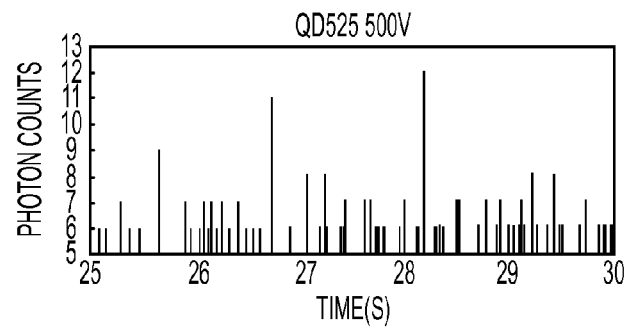
Figure 2D:
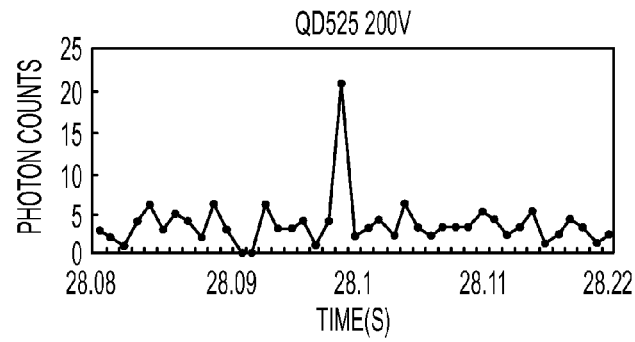

The nanofluidic device was fabricated on a 500 µm-thick UV grade fused silica wafer (Mark Optics, Santa Ana, Calif.) using standard photolithographic and etching techniques. A schematic layout of microfluidic channels is shown in FIG. 1. The detection channel has a width of 2 µm and CF4 plasma was used to dry etch the channel to the depth of 500 nm. A protective surface coating is then spin-coated onto the wafer and injection ports were drilled with high-speed sandblast tool. After removal of surface coating and a thorough piranha cleaning, a cover UV grade fused silica wafer of 170 µm is carefully clinched to the substrate wafer using DI water as intermediate. Permanent bonding is achieved by annealing the wafer at 1050 degree Celsius in air for 5 hours.

Protein molecule is notoriously known to stick to fused silica surface due to strong electrostatic interaction and the phenomenon is even worse in microfluidic channel, which has a high surface-to-volume ratio. Severe protein adsorption was observed in bare fused silica micro-channel and detection efficiency is extremely low. Various fused silica surface coating schemes were developed to alleviate or eliminate this problem for protein studies in microfluidic environment [42]. High-molecular-mass polyethyleneimine (PEI) coating was introduced by Bedia Erim and co-workers for separation of basic proteins and peptides by capillary electrophoresis [43]. PEI is a positively charged polymer and found to absorb irreversibly to the fused silica surface, even after flushing with strong acid or base [42]. In this experiment, a 0.5 (w/v) % PEI (Mw=10,000, Alfa Aesar, Ward Hill, Mass.) in IP buffer was prepared and coating procedure is simply flushing the micro-channel with PEI-added buffer overnight.

The fluorescence photon burst experiment was performed on an Alba Fluorescence Correlation Spectrometer (FCS)™ system by ISS Inc. (Champaign, Ill.). This system is equipped a 370 nm diode laser with an average power of 20 µW at objective. The schematic configuration of the system is shown in the FIG. 2. To ensure a good signal-to-noise ratio, a 63× Nikon water immersion objective with numerical aperture of 1.2 was used. The effective detection region is 0.5 µm in diameter, which is defined by the confocal pin hole size of the system. Sample in micro-channel is electrokinetically driven at various potentials. Fluorescence photon burst raw data is collected at a sampling frequency of 100 k for 50 seconds.

Quantum Dot 525 (QD525) conjugated goat anti rabbit antibody (Invitrogen) was used to characterize the detection of QD525 in the micro-channel. QD525 conjugated antibody (1 µM) was diluted in Immuno-precipitation buffer (IP buffer, 20 mM Hepes-KOH, 0.1 mM KCl, 2 mM $MgCl_2$, 15 mM NaCl, 0.2 mM EDTA, 1 mM DTT, 10% glycerol) in 1:5000 ratio. The sample was then loaded into the micro-channel for single fluorescence signal detection. For specific protein detection, Hemagglutinin (HA) epitope tagged MAX cDNA was transfected and overexpressed in HEK293 cell line. The cells were then lysed by RIPA lysis buffer and total cell lysates were collected to measure the protein concentration before subsequent analysis. 500 µg of protein lysate sample was diluted in IP binding buffer and made it to final total 1 ml.

500 μg of rabbit anti-HA tag primarily polyclonal antibody (Santa cruz, 200 mg/ml) was then added into the sample and rotated in 4° C. for overnight. Subsequently, 2 μl of QD525 conjugated anti-rabbit antibody (1 μM) was added into the sample and incubated in room temperature for 1 hour and then diluted 10 times in IP binding buffer. The sample was then loaded into the nano-channel for the single molecular detection.

Data Analysis

Traditional FCS analysis only yields an average information for a particular measurement of collective individual molecules [44-45]. If the sample is heterogeneous, valuable information of individual molecule could be masked by the average. This is usually the case when studying molecule-molecule interaction since bound/unbound ratio could vary significantly under different circumstances. Two-color cross-correlation was then developed at this point to improve the accuracy [44]. However, two-color will inevitably increase the complexity of the system and present new challenges for detection, such as excitation efficiency of different fluorescent labels, spectrum overlapping of two fluorescent labels, etc. In this invention, the inventors introduce an alternative way to present the information of individual molecules. A collective of photon burst events in a certain time span were first analyzed individually and a two-dimensional (2D) plot of photon burst width versus photon counts for each burst event was then generated. This could provide characteristic information of different molecules depending on their spatial locations on the 2D plot.

Figure 3A:
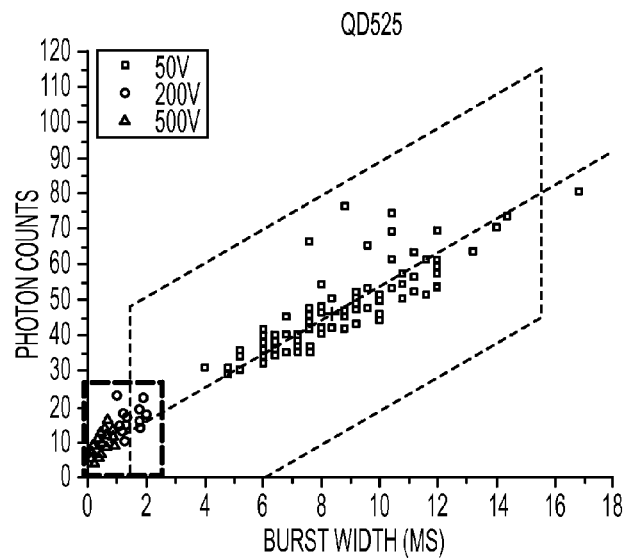
FIG. 3. 2D plot of QD525 conjugated antibody. (A) 50V, 200V, and 500V's QD525 distribution in 2D plot. (B) 250V and 500V's QD525 distribution in 2D plot. (C) Diagram of QD525 conjugated antibody.
Figure 3B:
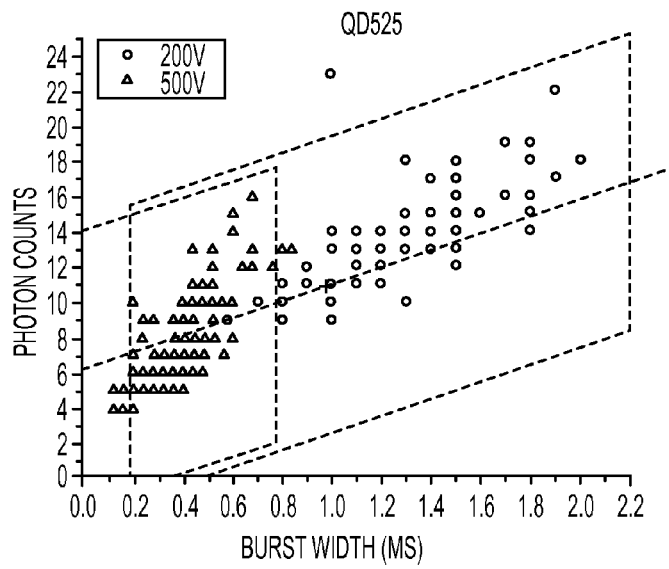
Figure 3C:
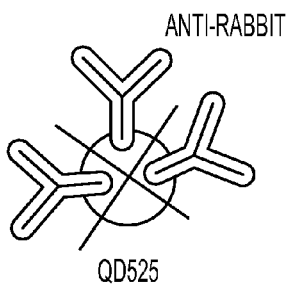
Figure 4A:
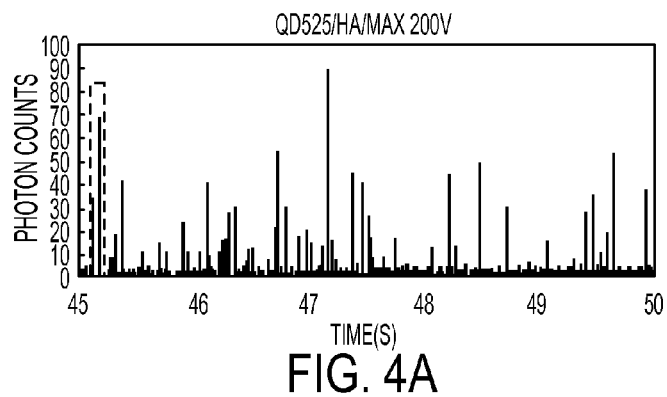
FIG. 4. Photon burst signal of QD525 in recognizing HA-MAX from mammalian cell lysate. (A, C) 200V and 500V's photon burst signal. (B, D) Amplified and normalized data of selected region in (A, C).
Figure 4B:
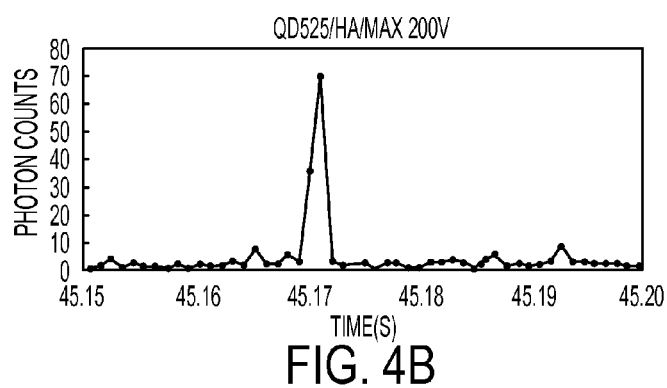
Figure 4C:
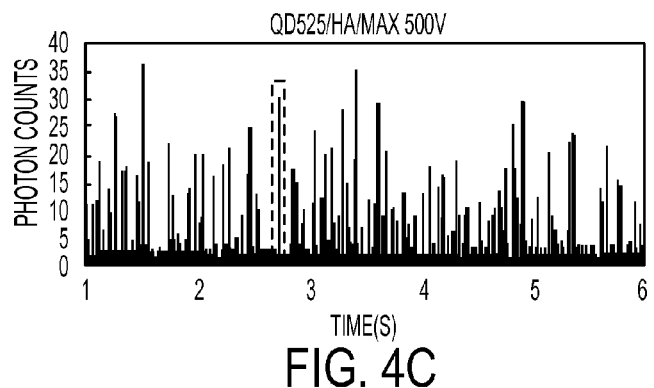
Figure 4D:
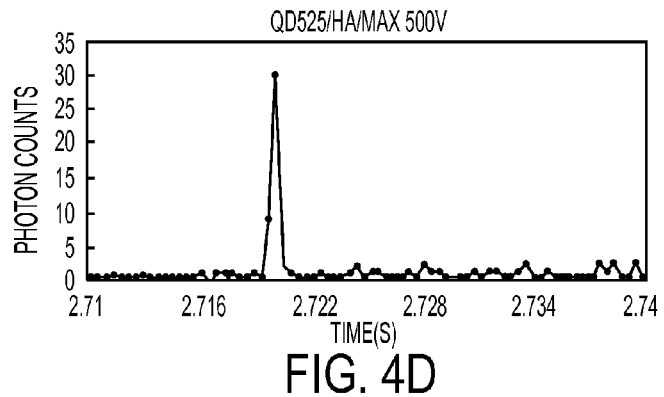

To get this 2D plot, control experiment of single QD525 conjugated secondary antibody (QD525) in micro-channel was first performed at different applied voltages and their respective autocorrelations were obtained with the ISS Vista™ software. After fitting the autocorrelation with the built-in flow model, the inventors obtained the average flow velocities of QD525 in micro-channel for different potentials. Since the inventors already knew the focal volume radius, the inventors could estimate the average residence time of QD525 in the detection volume. Thereafter, the inventors binned the photon burst data with a time, which was slightly longer than this residence time, to ensure single molecule resolution. After binning, the inventors extracted the raw data (ASCII format) of photon burst signals and calculate the average intensity with standard deviation ($\sigma$) for a particular measurement. Since the inventors assumed photon burst follows Poissonian Distribution [26], the $\sigma$ was calculated to be square root of average intensity. To identify the individual molecule, the inventors set the photon burst threshold value to average+3*$\sigma$[1]. Intensity higher than the threshold was identified as signal while those below the threshold was considered as noise. Once the position of the signal was determined, the inventors went back and re-binned the photon burst raw data with a different time, which was 10 times shorter than the previous bin time. In this newly-binned photon burst data, the previous identified signal was located and its photon burst width in time and total counts were obtained to generate the 2D plot (FIG. 3). This process was repeated for different burst signals and more than 100 data points for each condition were recorded. The same data analysis procedure was also performed on QD525 in HA-MAX protein detection data (QD525-HA-MAX). The inventors assumed that the change of fluid viscosity in both QD525 and QD525-HA-MAX were negligible and residence time of QD525 obtained from the autocorrelation of QD525 alone is also valid for the latter case as well.

Results and Discussions

Among conventional bio-analytical techniques, immunoassays are commonly used to detect specific protein and assess protein-protein interaction present in cell extracts. Taking advantage of miniaturized devices, the technique described in this article offers a simple, fast and accurate immunoassay, which only needs small amount of sample. However, without surface treatment, severe surface adsorption of proteins was observed in fused silica nanofluidic channel, which seriously interrupted the detection. After surface modification by using positively charged PEI polymer, it significantly increased the signal at detection region and the inventors were able to detect sufficient molecules for analysis during the reasonable time span. Thus, this surface treatment protocol is a crucial process in developing this immunoassay technique. In addition, sample concentration used in this experiment is at least two orders of magnitude lower than concentration, where on average only one molecule is calculated to be in the focal volume at one time. This ensures the single molecule resolution the inventors need for our data analysis to be valid. Similar to conventional immunoassay, the inventors utilize the interaction between antibody and antigen and the ability of antibody recognizing specific antigen. Polyclonal antibodies are able to recognize a variety of epitopes on a single antigen. For this immunoassay, the inventors chose to use is polyclonal primary antibody (rabbit anti-HA) and the inventors expect multiple primary antibodies will bind to one detection target, i.e. HA-MAX, in the mixture of breast cancer cell lyses. The fluorescent tag QD525 is bound to the primary antibody through a secondary antibody. There is relatively high probability that one HA-MAX protein complex is associated with multiple QD525s based on the relative concentrations for each specie. Therefore, from 2D plot the inventors can identify HA-MAX complex in the mixture of QD525 target un-bound or bound proteins based on the fluorescent photon counts for each individual event.

Baseline data were first obtained with QD525 conjugated secondary antibody alone in the fluidic channel. Photon burst histories in a time span of 5 seconds were recorded at 50V, 200V and 500V (FIG. 2). The raw data were binned at 8 ms, 1 ms and 400 μs for 50V, 200V and 500V, which based on the calculation of the residence time of QD525 in the detection volume under different potentials. According to Poissonian distribution, the photon burst thresholds were calculated as 35.1±0.56, 7.58±0.09 and 4.73±0.05 for 50V, 200V and 500V, respectively. For a better visualization, the inventors set the counts minimums to be 36.8 and 5 for the photon bursts at 50V, 200V and 500V, respectively. FIG. 2 shows a close-up look at a particular QD525 event for 200V. As the inventors expect, the QD525 flows positively correlate with the potential intensity, which results in more events been detected in a same time span under high potential, i.e., at higher potential, individual molecule spends less time in the focal volume. Thus, photon count for each event decreases when voltage increases. With these photon burst raw data, 2D plot for QD525 including all three potentials was generated (FIG. 3) and a least square linear fit was then performed. Consequently, the slope of the linear fit is the average photon counts per bin, which is around 4.72 per millisecond. This average photon counts per bin is later used for determining the boundaries for QD525 regimes in 2D plot. Since the laser spot is smaller than the fluidic channel width in this experiment, different spatial pathway will lead to photon counts and burst width fluctuations for an individual molecule as it passes the focal volume. Furthermore, variations in QD525 flow velocity will also introduce additional fluctuations in both dimensions. To account for these fluctuations, the average and standard deviation of photon counts and burst width (assuming a normal distribution) are calculated at each potential. The boundaries of QD525 regime are set to be the average plus/minus three times the standard deviation for both the photon counts and burst width. The inventors then apply the slope when the boundary values for both dimensions are determined, i.e., the average photon counts per bin set the QD525 regimes for each potential, which are illustrated in dashed parallelogram in FIG. 3. The purple cross in each parallelogram represents the average point for each potential in terms of photon counts and burst width.

Figure 5A:
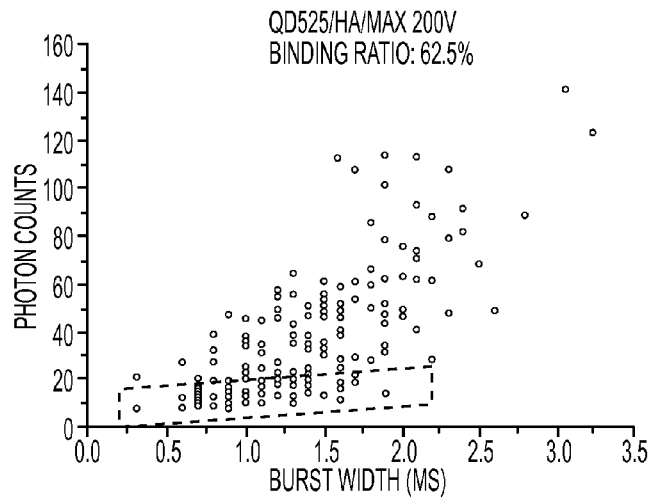
FIG. 5. 2D plot of Q0525 in recognized HA-MAX. (A) 20 plot of 200V's QD525 signal distribution. (B) 500V's QD525 signal distribution plotted in 2D. (C) Diagram of QD525 in recognized HA-MAX.
Figure 5B:
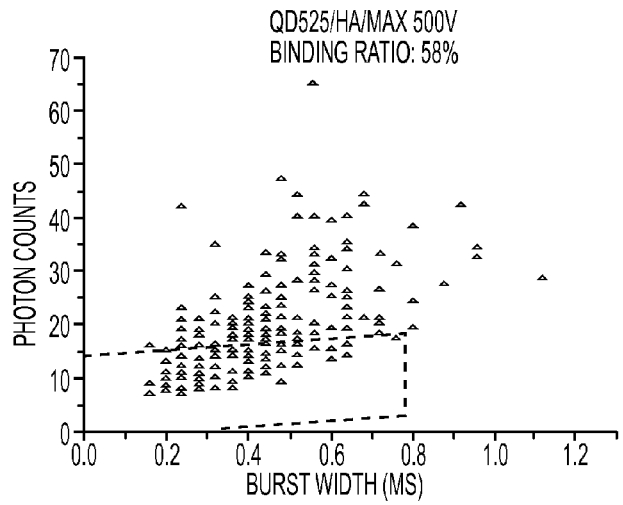
Figure 5C:
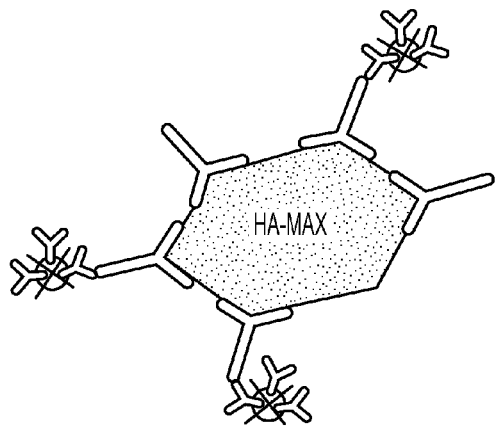
Figure 6:
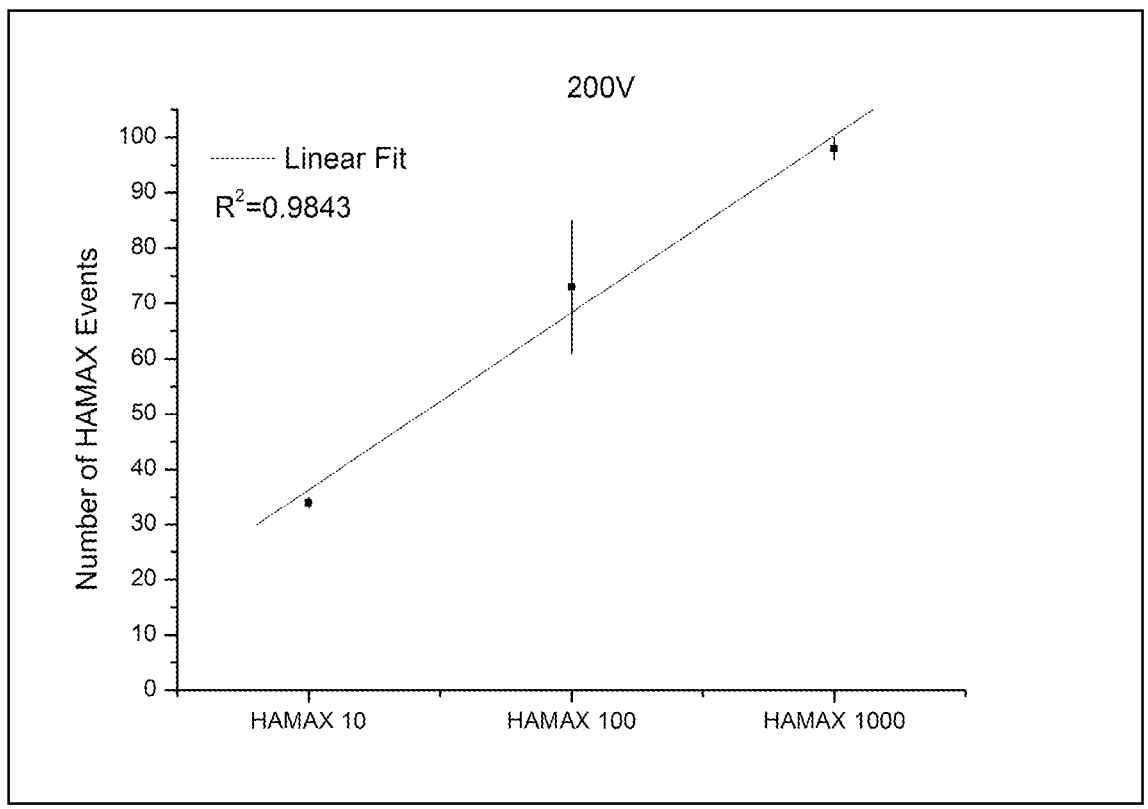
FIG. 6. HAMAX events as a function of cell lysate concentration. HAMAX 10: 10 microgram cell lysate in 1 ml IP buffer; HAMAX 100: 100 microgram cell lysate in 1 ml IP buffer; HAMAX 1000: 1000 microgram cell lysate in 1 ml IP buffer FIG. 7. HAMAX concentration analysis—HAMAX events. Excellent linear relationship found for number of HAMAX events as a function of HAMAX transfection DNA amount.
Figure 7:
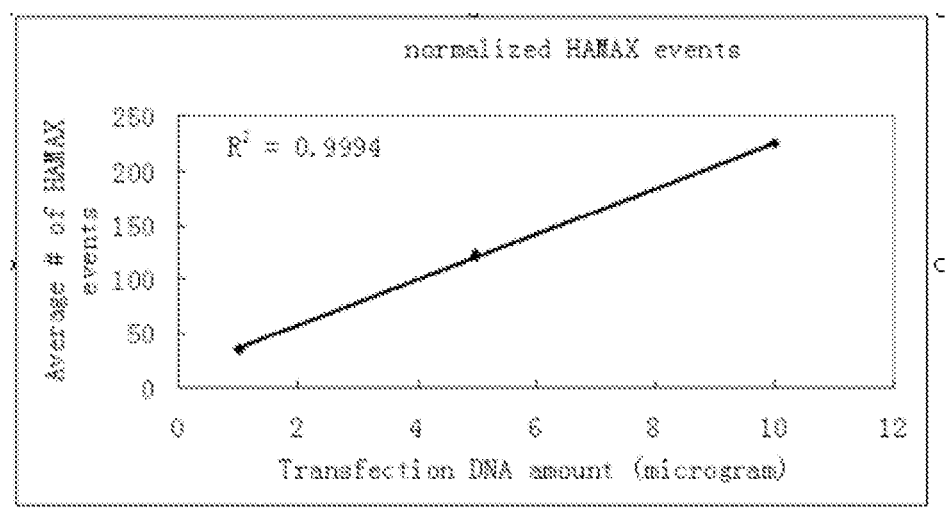
Figure 8A:
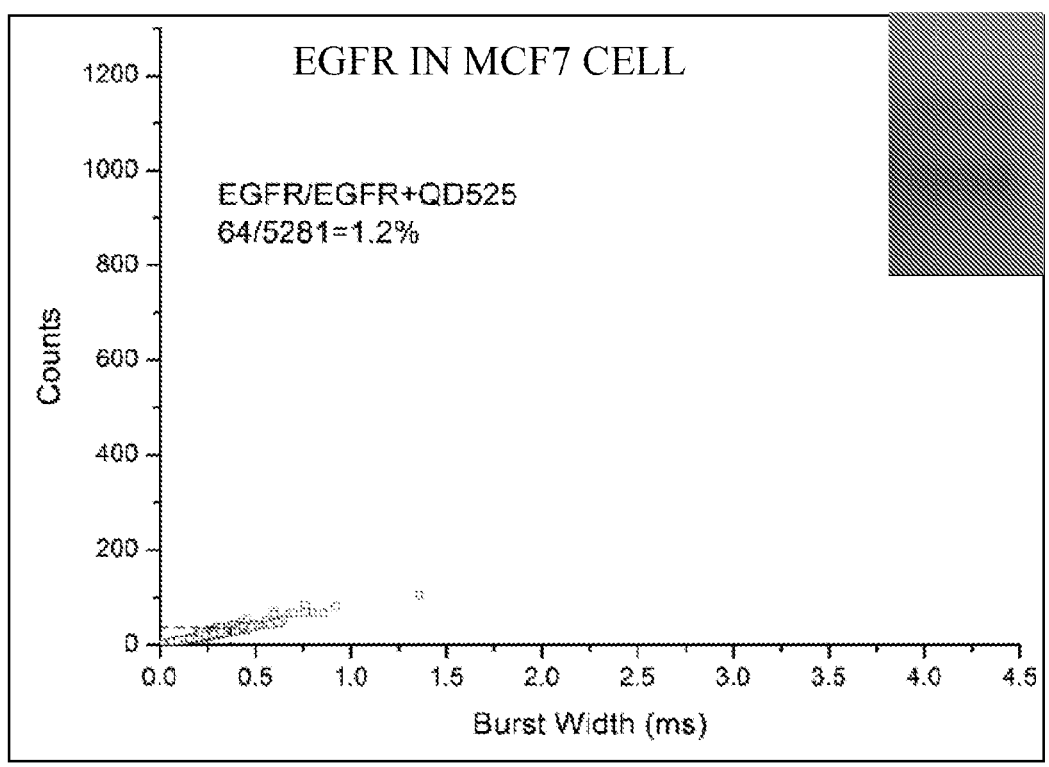
FIG. 8. EGFR expression in endogenous level. Conventional study shows different cells express EGFR protein at a different level. For example, 468 cell exhibits a high level of EGFR expression comparing to MCF7, as shown by the western blot at the bottom. This result is also confirmed by the our 2D photon burst analysis.
Figure 8B:
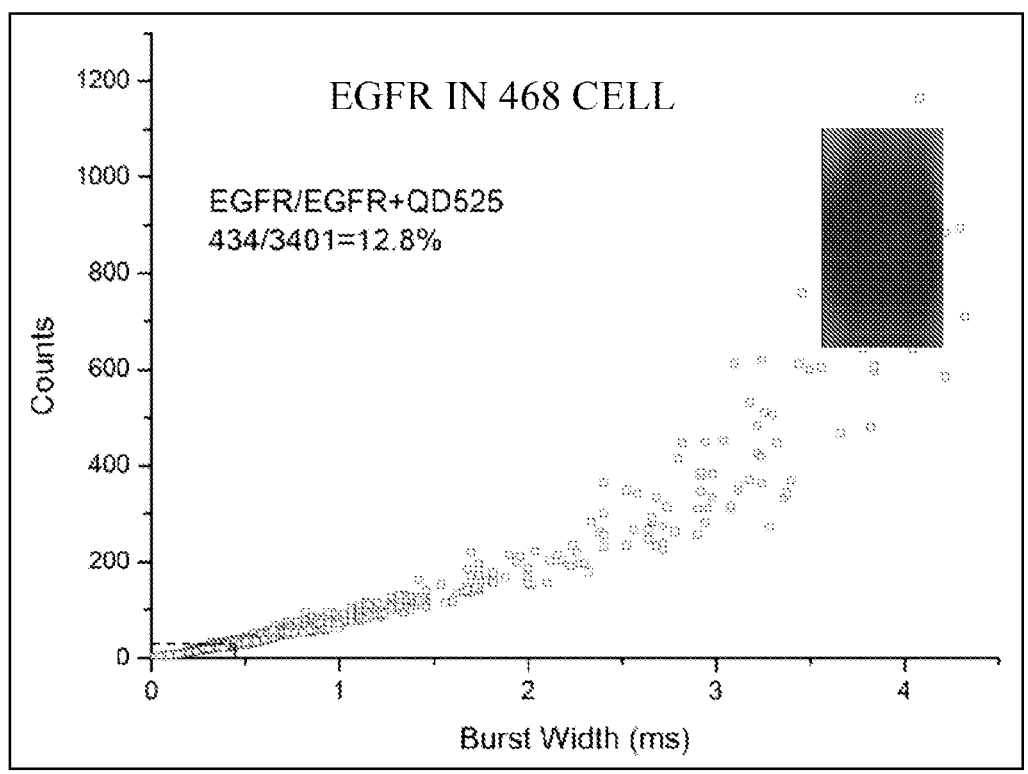
Figure 9A:
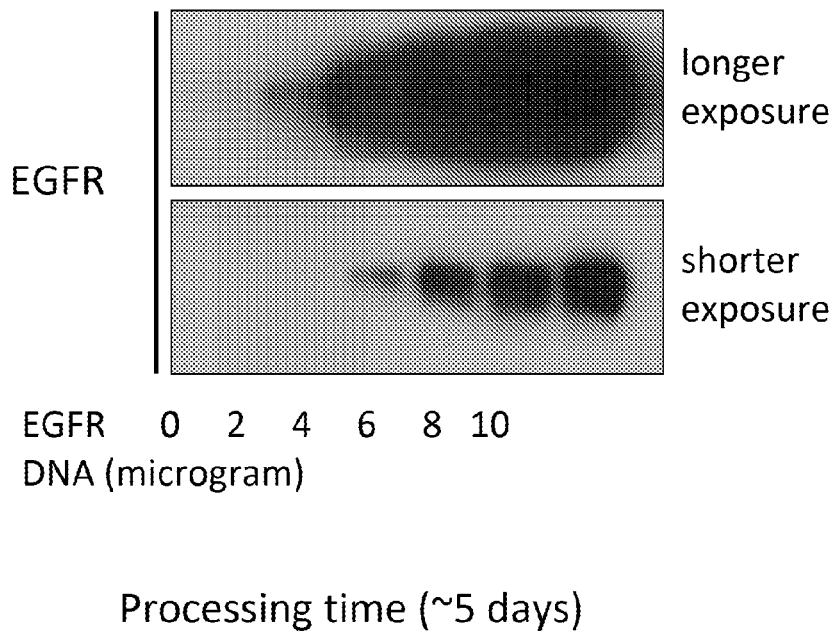
FIG. 9. EGFR concentration analysis. Similar as the HAMAX concentration analysis, the inventors transfected EGFR DNA into 293 cell to over-express EGFR proteins. More transfection DNA leads to cell expressing more EGFR proteins, thus a higher concentration. An excellent linear relationship is found for EGFR events as a function for EGFR transfection DNA amount FIG. 10. Dual-color photon burst coincidence analysis for three-protein SRC/EGFR/STAT3 interaction detection—endogenous level FIG. 11. RC/EGFR/STAT3 interaction dynamics in endogenous level. EGFR, STAT3, SRC-1 protein, 73.5%-87.8%; EGFR/STAT3, EGFR/SRC—2 protein complex, 9.6%-11.2%; SRC/EGFR/STAT3—3 protein complex, 0.6%-1%.
Figure 9B:
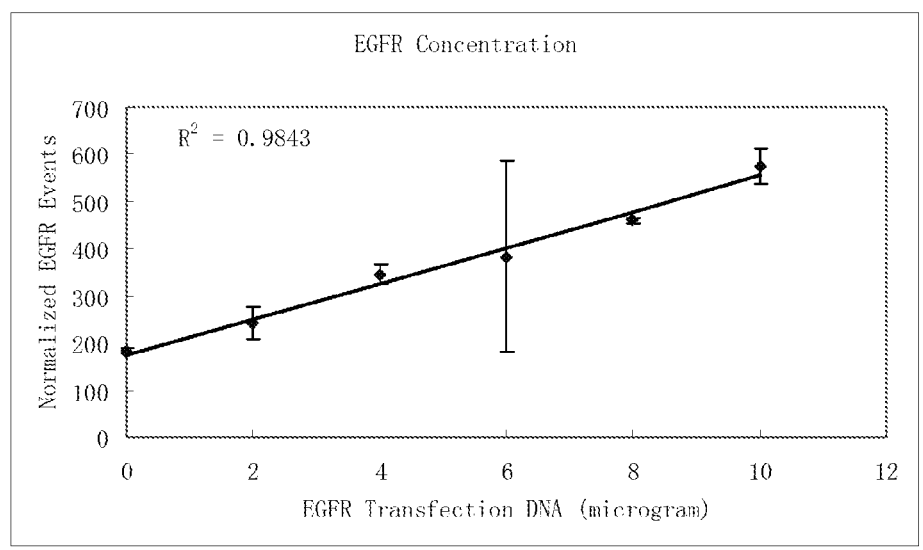
Figure 10:
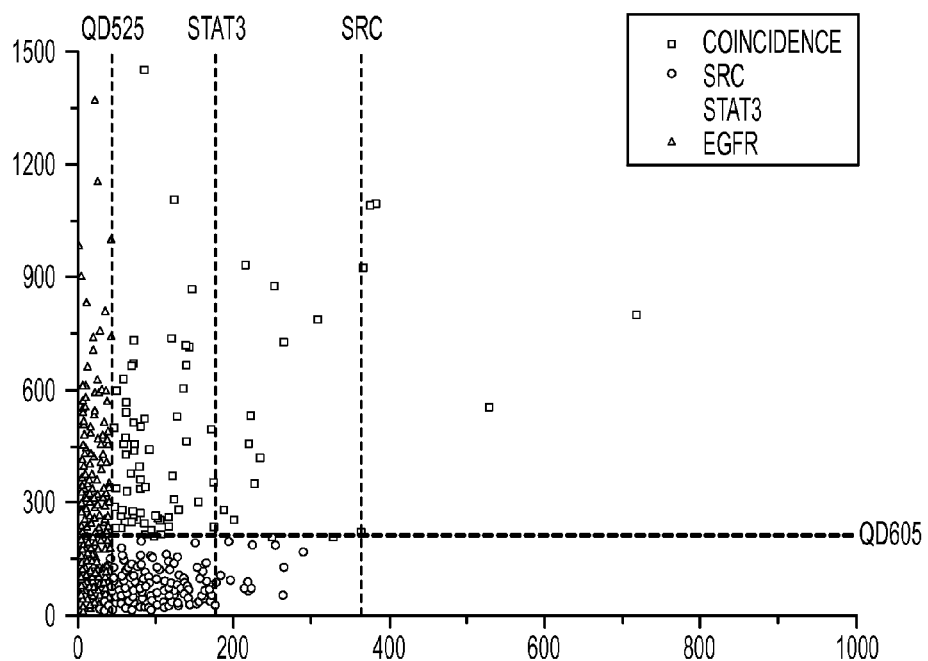
Figure 11:
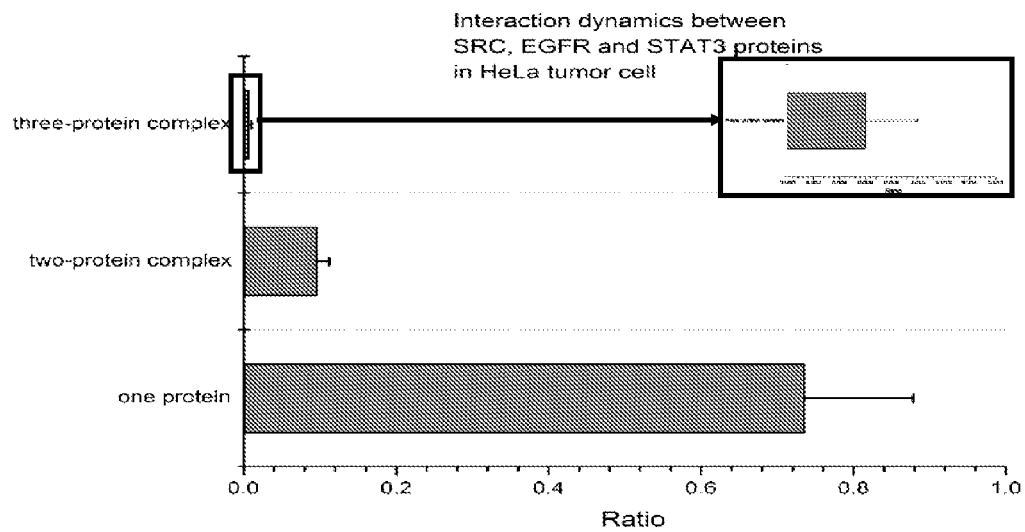
Figure 12A:
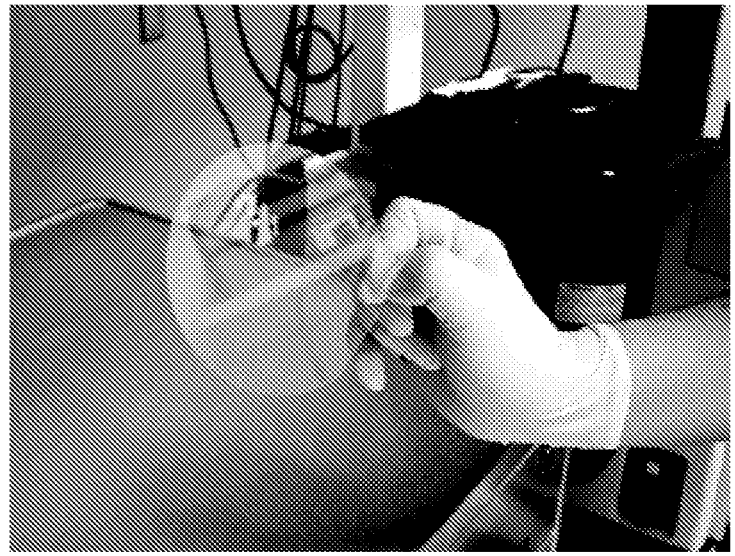
FIG. 12. Fused silica micro/nano-fluidic channel. A. Micro/nano-fluidic channels fabricated on UV-grade fused silica wafers. B. Optical image of microchannel. Cross section SEM image of fused silica channel with a depth of 100 nm.
Figure 12B:
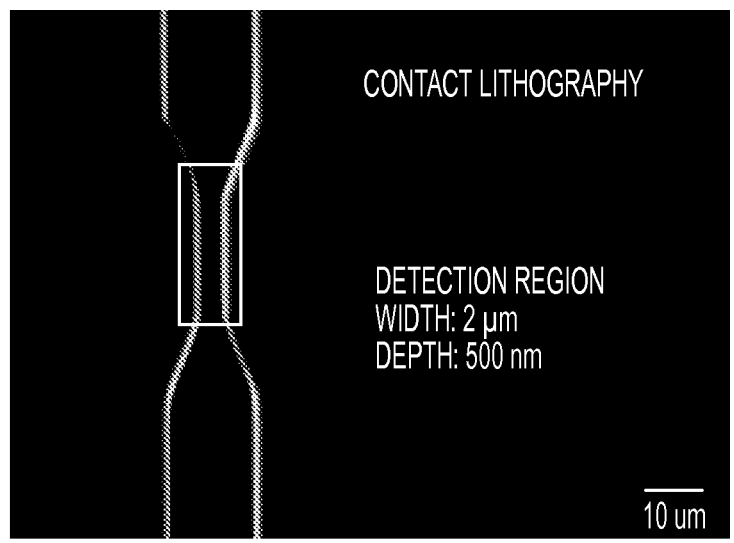
Figures 12C, 13:
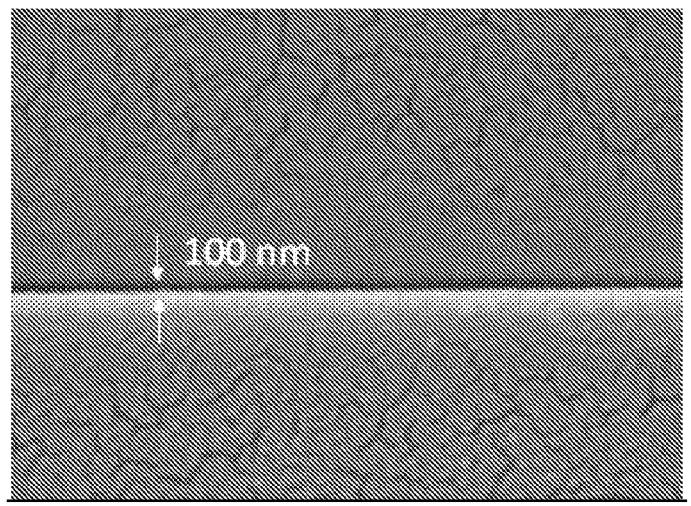
FIG. 13. Micro/nano-fluidic channel device fabrication process flow.
Figure 14A:
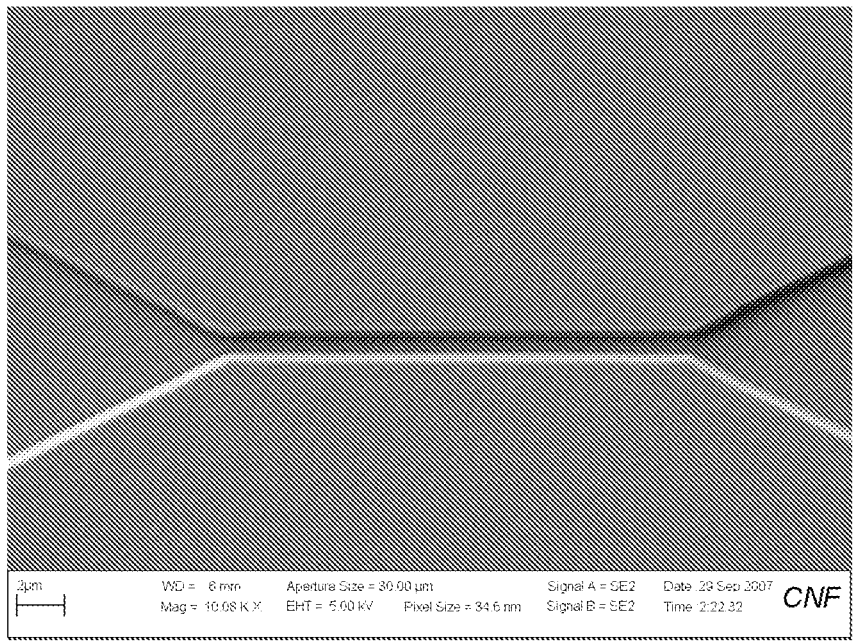
FIG. 14. SEM images of nanochannels by advanced lithography techniques. A. Projection photolithography (Top View). B. E-beam lithography (Cross Section).
Figure 14B:
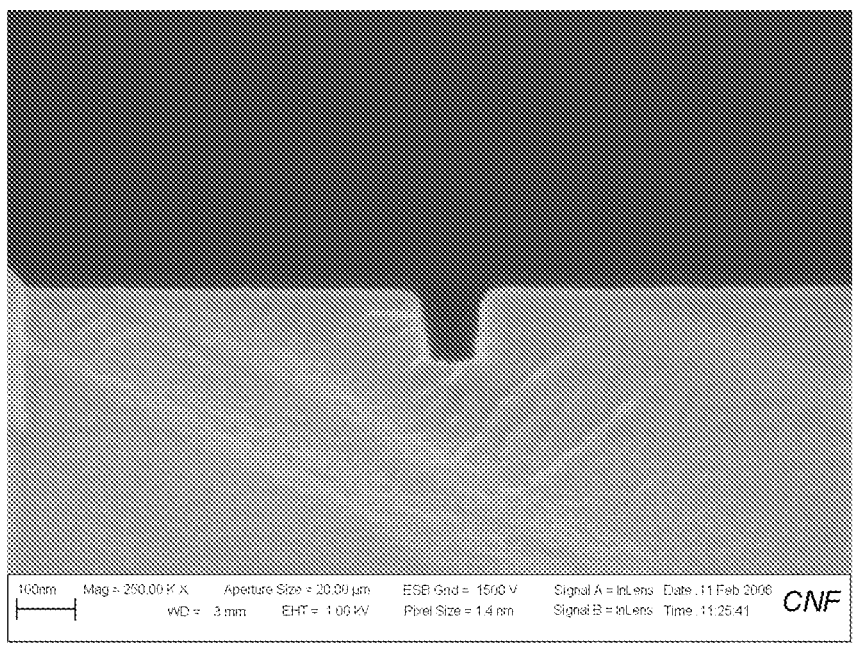
Figure 15:
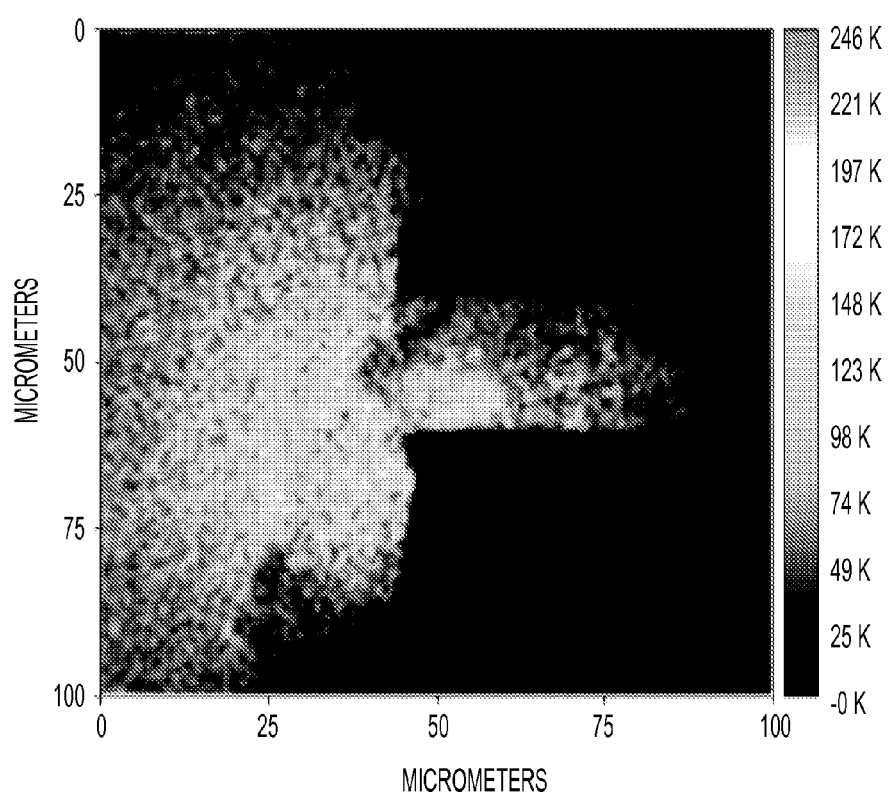
FIG. 15. Fluorescence image of QD525 filled fused silica channel at solution inlet and channel entrance. It shows severe protein adsorption on fused silica surface. Without PEO (polymer coating) on the nanochannel surface, target protein and protein complexes cannot be detected. This is the fluorescent image of protein adsorbed on the nanochannel surface without PEI coating. If the channel is coated with PEI, there is no protein adsorbed on the channel surface.
Figure 16:
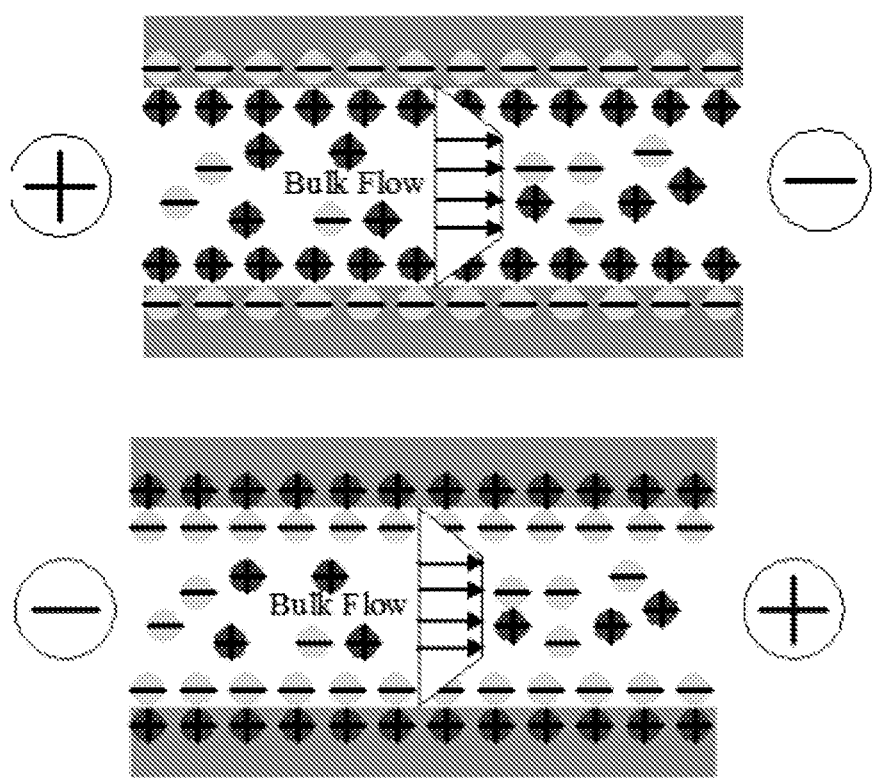
FIG. 16. Electro-osmotic flow in fused silica channel. A. Bare fused silica channel with aqueous solution. B. PEI coated fused silica channel with aqueous solution. The flow direction of Qdots (towards positive electrode) suggests a positively charged channel surface and a successful PEI surface coating.
Figure 17:
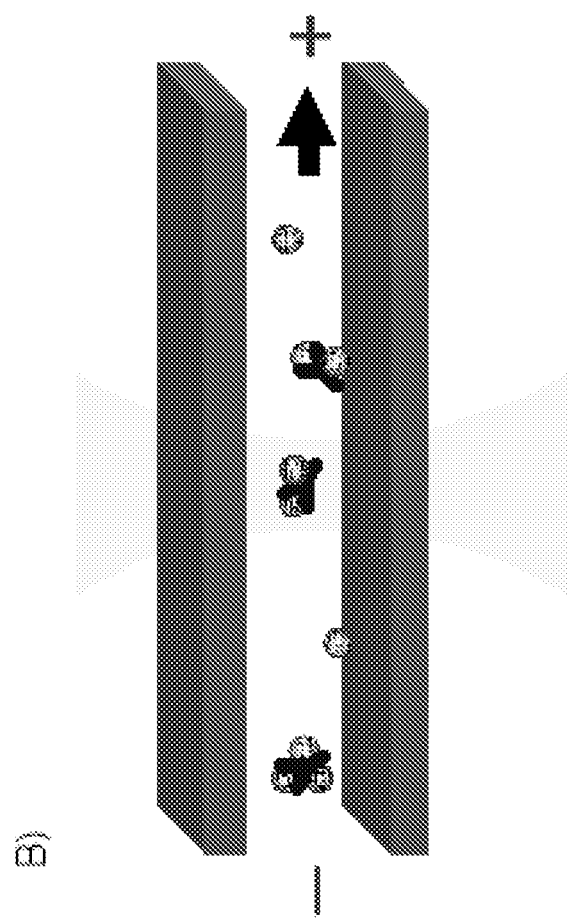
FIG. 17. Micro/nano-fluidic fluorescence single molecule detection. Proteins and their complex labeled with Quantum Dots are introduced into the fluidic channel by capillary force and electro-kinetically driven by an external voltage source. A diode Laser of 375 nm excites Qdots-labeled proteins as they are passing through the focal volume and their fluorescence signal are detected by Avalanche Photodiode (APD). QD surface biomolecule with Sulfur atom, anti-rabbit with sulfur atom at the end. Conjugation based on S=S covalent bonding.
Figure 17:
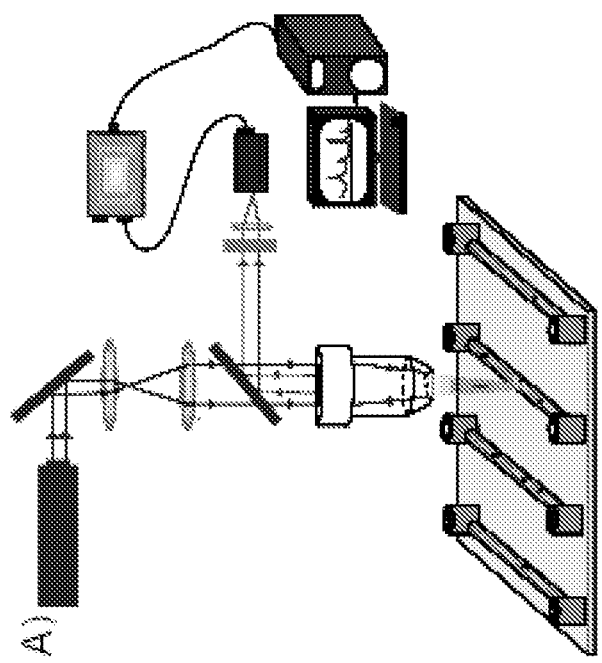
Figure 18:
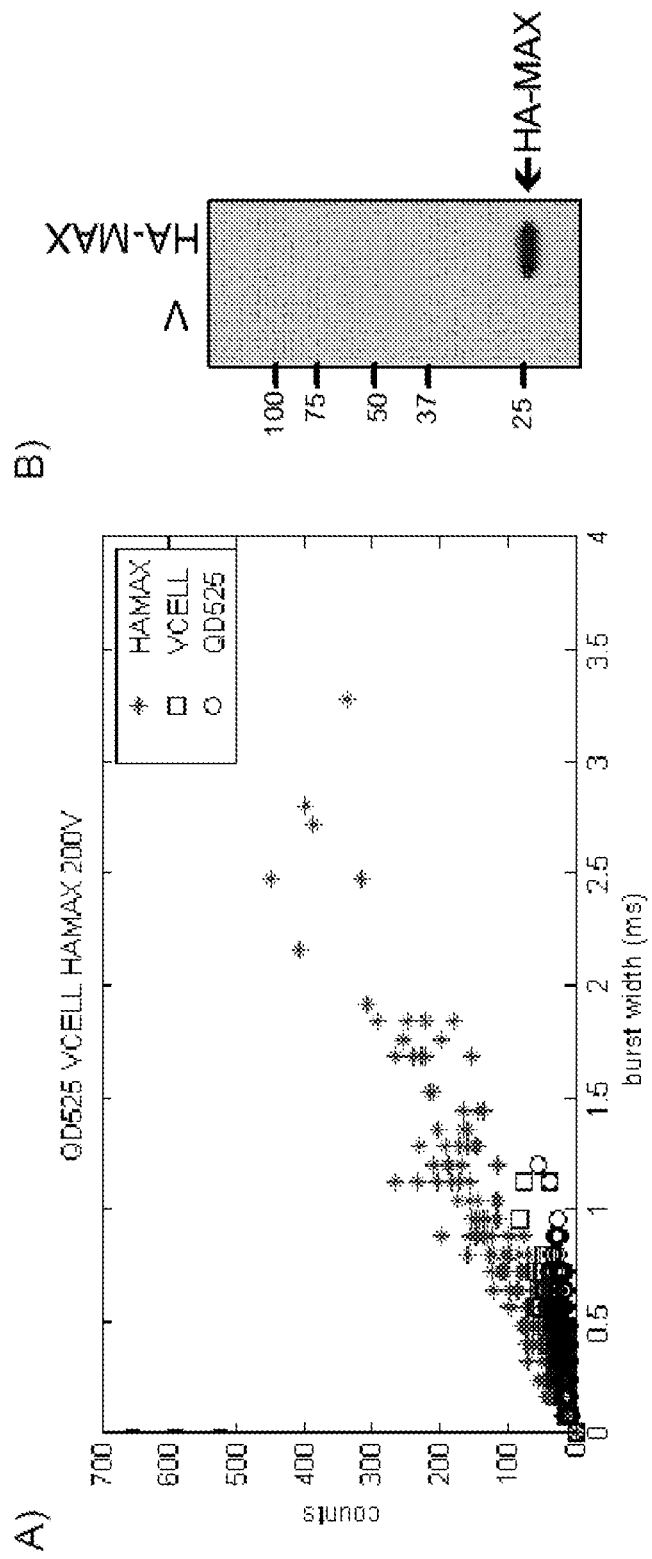
FIG. 18. Distribution of events from HAMAX sample in 2D photon burst plot shows significant difference (high-count events) from the vector and QD525 samples, indicating the detection of HAMAX protein. Vector and QD525 sample shows similar distribution, which suggests no significant non-specific binding of anti-HA to proteins other than HAMAX. Existence of HAMAX protein is also confirmed by conventional western blot.
Figure 19A:
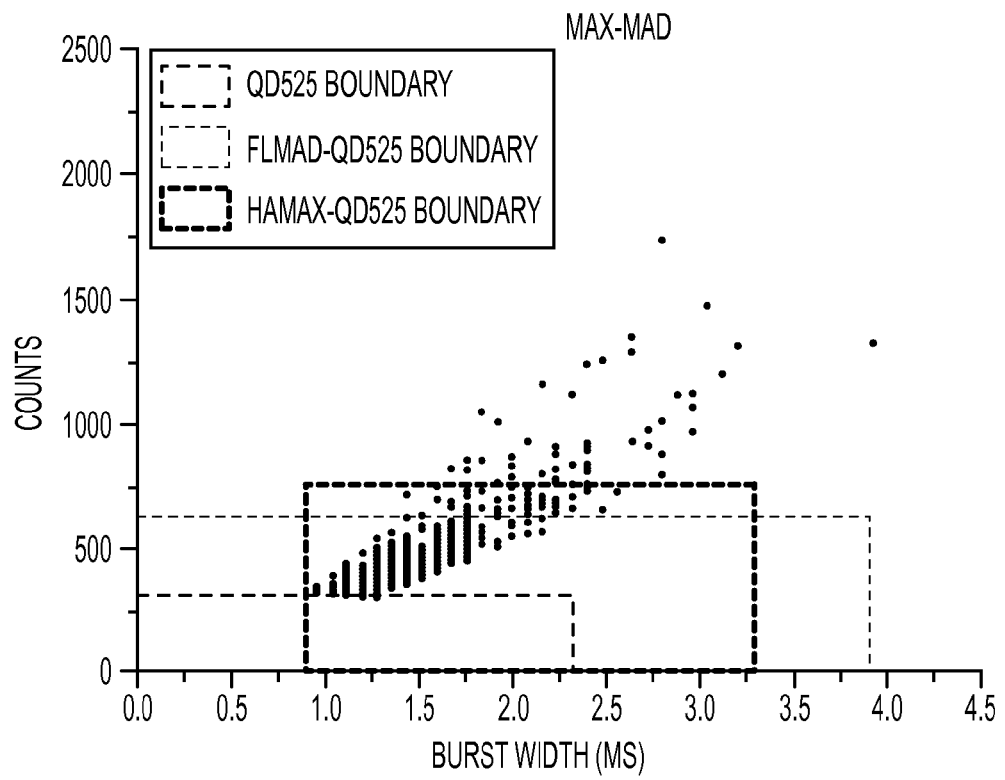
FIG. 19. One-color detection of MAX-MAD interaction. Among all the identified MAX and MAD proteins, 7%-10% are forming MAX-MAD complex.
Figure 19B:
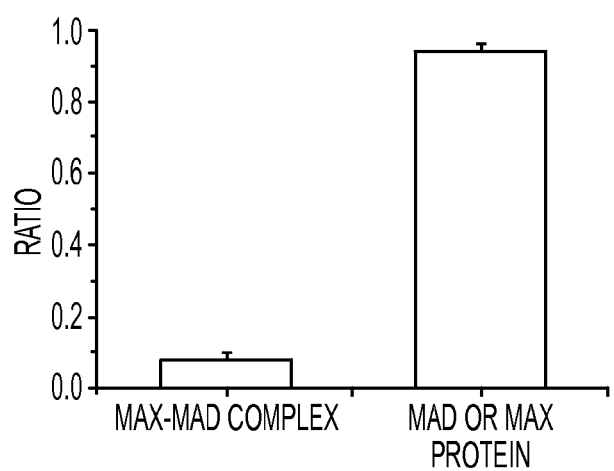
Figure 20A:
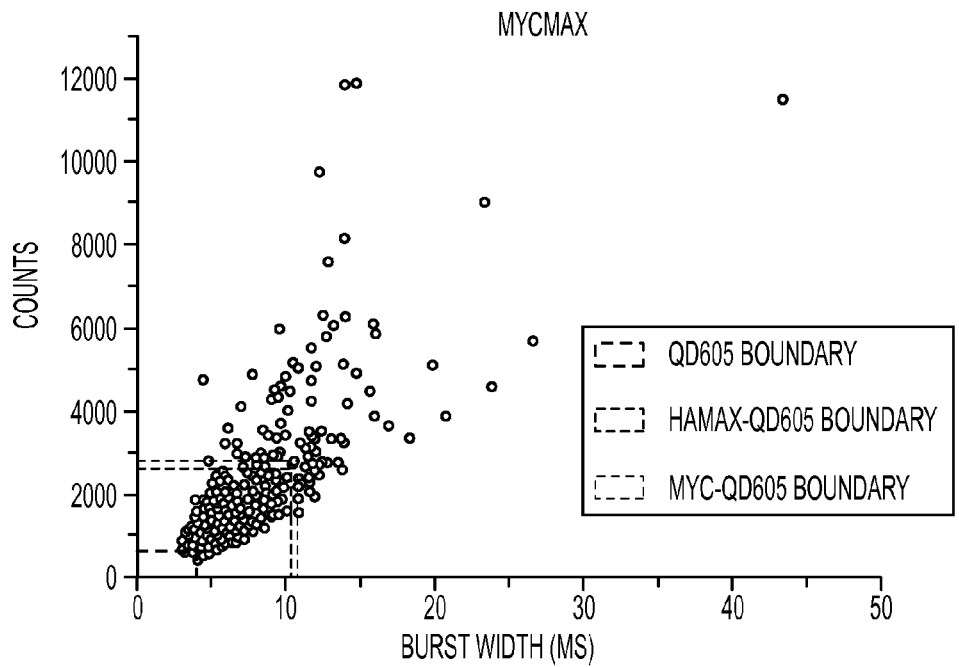
FIG. 20. One-color detection of MAX-MYC interaction. Among all the identified MAX and MYC proteins, 7%-8.1% are forming MAX-MYC complex.
Figure 20B:
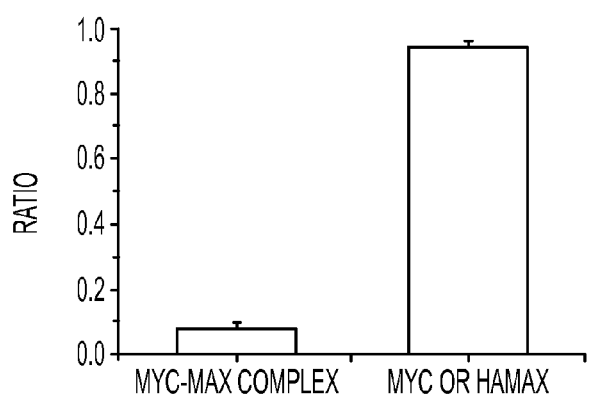
Figure 21:
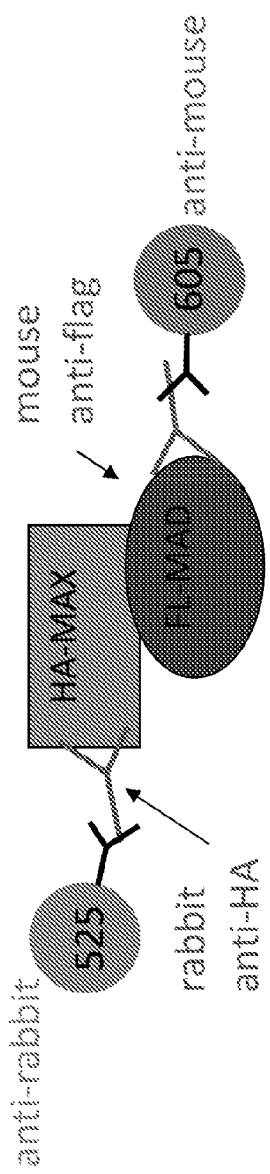
FIG. 21. Model protein interaction—two-color scheme. Detection of Qdot-conjugated protein-protein interaction.
Figure 21:
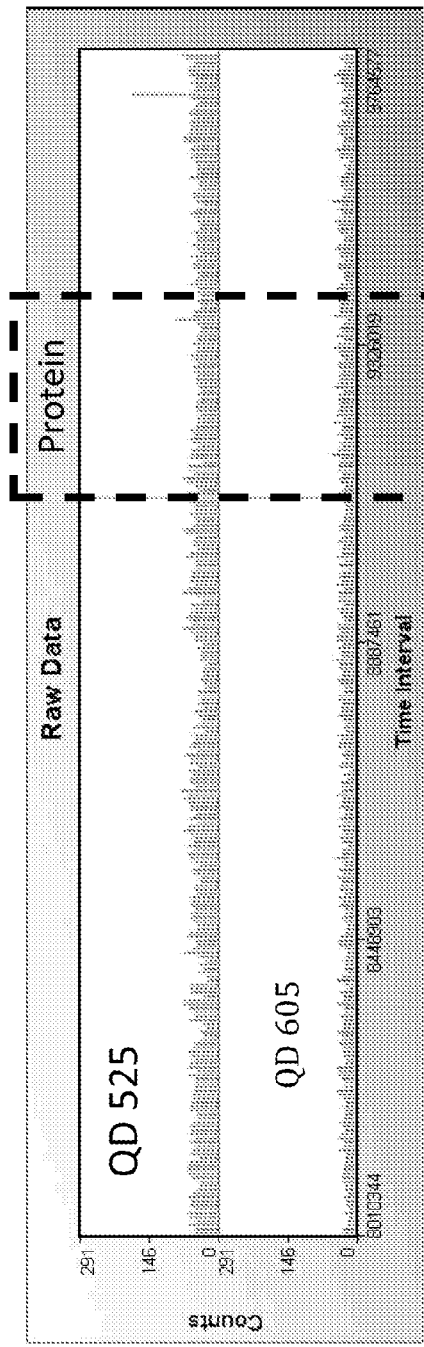
Figure 22A:
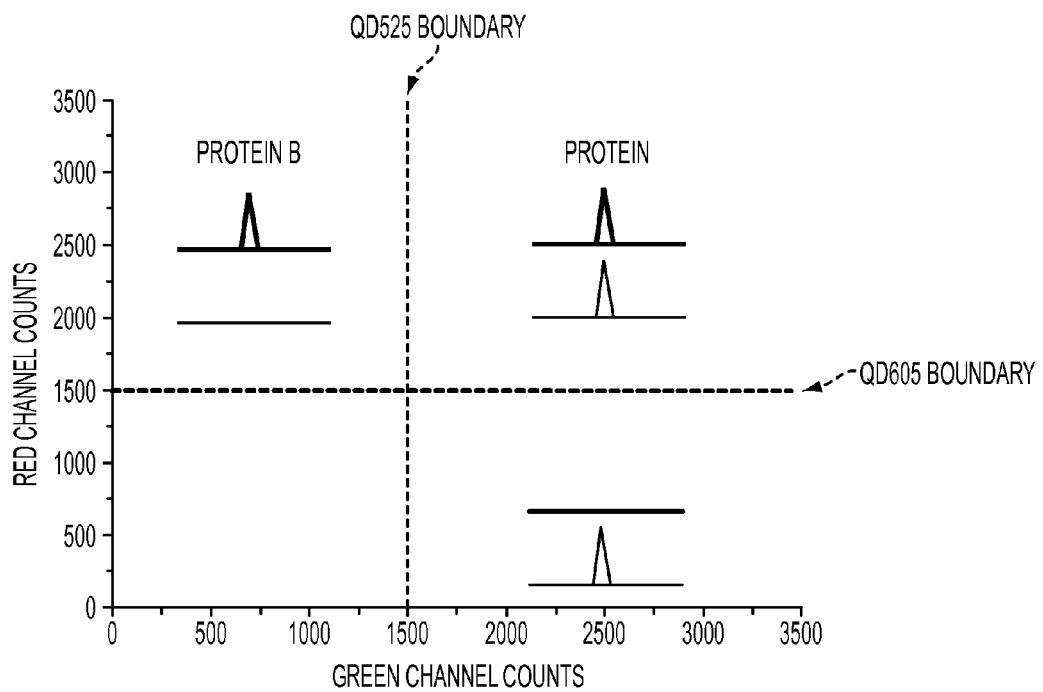
FIG. 22. Dual-color photon burst coincidence analysis. Dynamics about Ratio of interaction between protein A and B are determined by interaction analysis.
Figure 22B:
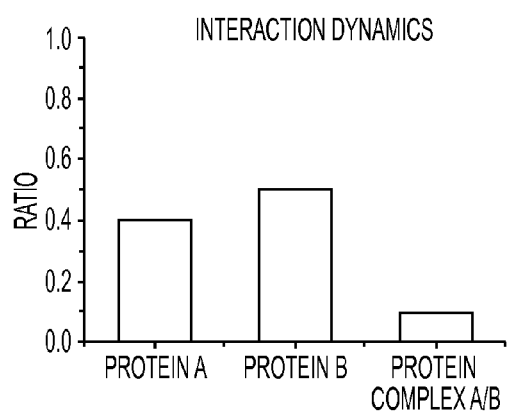
Figure 23:
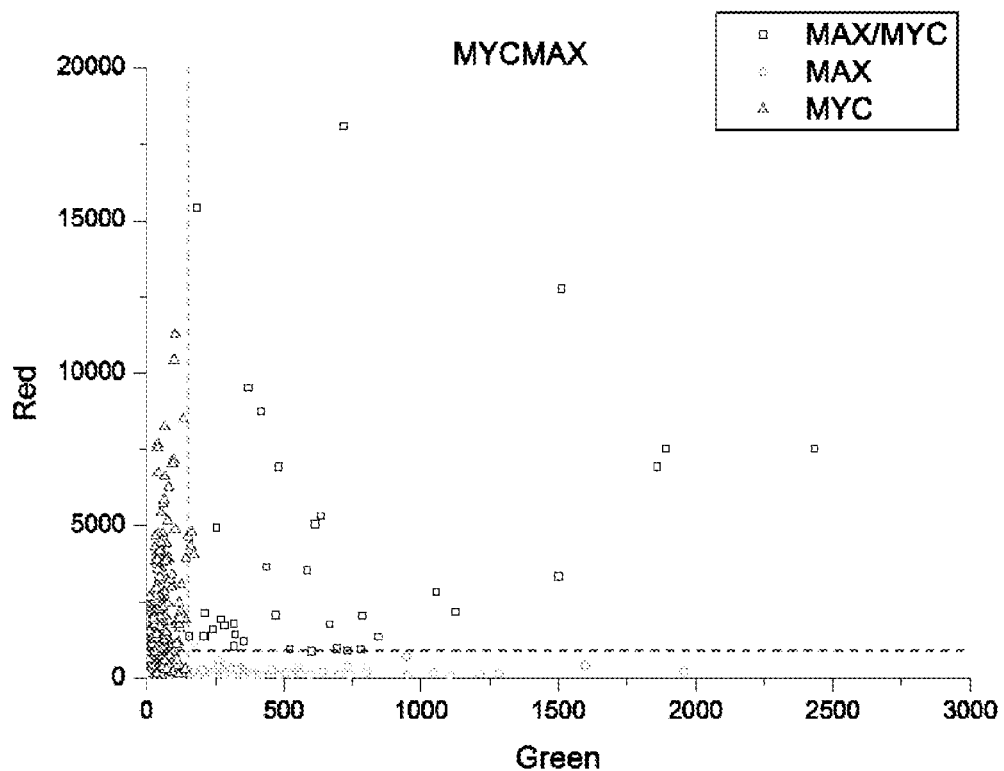
FIG. 23. Dual-color detection of MYC-MAX interaction. Among all the identified MAX and MYC proteins, 6.8-8.2% are forming MAX-MYC complex with the dual-color detection scheme. The MYC-MAX interaction dynamics obtained from one-color (7-8.1%) and dual-color (6.8-8.2%) detection schemes are in very good agreement.
Figure 23:
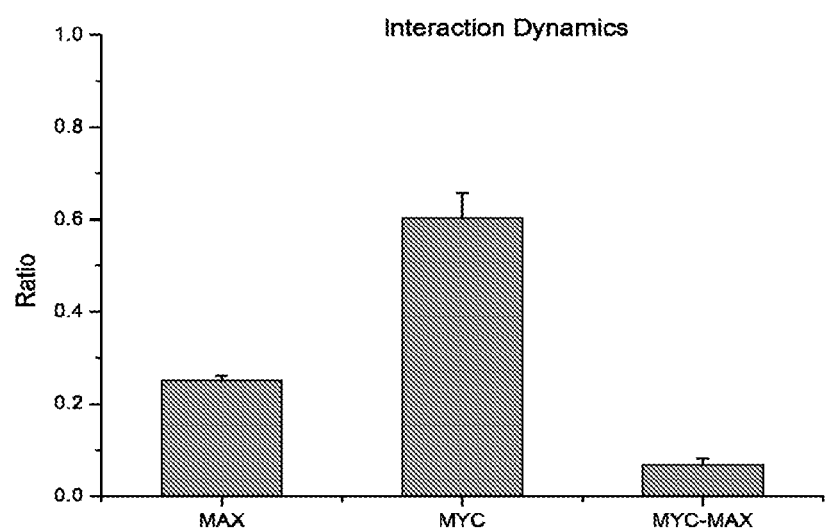

With the same fluidic channel, a mixture of molecules including HA-MAX transfected mammalian cell lysate, QD525/anti-rabbit secondary antibody, rabbit anti-HA primary antibody, was analyzed under similar conditions as for the previous QD525 experiment. FIG. 4 shows the photon burst histories of the mixture at 200V and 500V. Same bin times from previous QD525 experiment for 200V and 500V were used for the mixture sample and similar behaviors were observed in terms of photon burst and number of events as a function of voltage. However, one difference occurred that the number of photon counts for individual event was significantly higher and the signal-to-noise has improved tremendously as well. To further quantify this difference, 2D plots of HA-MAX mixture sample were obtained for 200V and 500V, as shown in FIG. 5. The cartoon in FIG. 5*c* illustrates the polyclonal nature of the interaction between rabbit anti-HA and HA-MAX, which allows us to distinguish HA-MAX complex events from free QD525 events in the mixture sample. In compare to the HA-MAX sample with the baseline data (QD525 alone regimes), it is obvious that the inventors detected HA-MAX protein complex since large number of events are locating outside the QD525 regime. For a total of 200 continuous events, 62.5% and 58% of the events were identified as HA-MAX in 200V and 500V, respectively. As the inventors expected, the percentages are reasonably closed under the two potentials. It's worthwhile to note that the inventors did observe some variations in photon per bin at different voltages, which causes an unwanted broadening of photo-counts and burst width distribution on the 2D plot. Thus, the inventors believe, mainly due to the non-uniform excitation of QD525. Since the laser spot is smaller than the channel when QD525 passed through the focal volume, different spatial pathway leaded to non-uniform excitation in both photon counts and burst width. There are several options the inventors can optimize the detection system. Currently, experiments are underway using nanofluidic channel with dimensions smaller than the laser spot. This could not only guarantee a uniform excitation, but also increase the detection efficiency due to all the molecules could be detected. The inventors could also sacrifice our laser power for a larger spot size if the same fluidic channel is to be used. Meanwhile, the inventors can substitute QD525 with QD605, which has higher excitation efficiency at the wavelength of our system [46].

The inventors have developed a microfluidic based single molecule flow proteometry for detecting specific protein in lysed mammalian cultured cell. A surface modification protocol also was developed to reduce protein adsorption to fused silica, in which significantly improved our detection efficiency. Unlike the conventional immuno-detections, the relatively high sensitivity and selectivity of this technique allow us to use very small amount of sample with no purification steps requirement for detection. Analysis time was reduced tremendously with this assay as well. In addition, the inventors introduced the concept of two-dimensional plot for data analysis. Each individual event is located on the 2D plot based on its photon counts and burst width. Approximately 60% of the events were positively identified as HA-MAX protein from the 2D plot. The coordinates of individual event on 2D plot could potentially serve as a molecular fingerprint of mass-to-charge ratio for different fluorescent molecules or complex as they are electrokinetically driven through the excitation volume. Thus, the detection scheme described together with the 2D plot analysis would offer considerable advantages over current bio-analytical techniques in identifying specific target proteins.

REFERENCES

The following references, to the extent that they provide exemplary procedural or other details supplementary to those set forth herein, are specifically incorporated herein by reference.

1. Petra S. Dittrich, Andreas Manz, Anal. Bioanal. Chem., 382, 1771-1782, 2005.
2. S. Weiss, Science, 283, 1676 (1999)
3. Shimon Weiss, Nature Structural Biology, 7(9), 2000, 724-n9
4. Darwin R Reyes, Dimitri Iossifidis, Pierre-Alain Auroux, Andreas Manz, Anal. Chem. 2002, 74, 2623-2636
5. Pierre-Alain Auroux, Dimitri Iossifidis, Darwin R. Reyes, Andreas Manz, Anal. Chem., 2002, 74, 2637-2652
6. Torsten Vilkner, Dirk Janasek, Andreas Manz, Anal. Chem. 2004, 76, 3373-3386
7. H. A. Stone, A. D. Stroock, A. Ajdari, Annu Rev. Fluid. Mech., 2004, 36; 381-411
8. Jonas O. Tegenfeldt, Christelle Prinz, Han Cao, Richard L Huang, Robert H. Austin, Stephen Y. Chou, Edward C. Cox, James C. Sturm, Anal. Bioanal. Chem. 2004, 378: 1678-1692
9. Todd M. Squires, Stephen R Quake, Reviews of Modern Physics, 77, 2005, 977-1026
10. Andrew J. de Mello, Lab Chip, 2003, 3, 29N-34N
11. H. Craighead, Nature, 442, 387 (2006)
12. J. T. Mannion and H. G. Craighead, Biopolymer, 85(2), 2006, 131-143
13. J. Han and H. G. Craighead, J. Vac. Sci. Technol. A, 17(4), 2142 (1999)
14. J. Han and H. G. Craighead, Science, 288, 1026 (2000)
15. S. W. Turner, A. M. Perez, A. Lopez and H. G. Craighead, J. Vac. Sci. Technol. B, 16(6), 3835 (1998)
16. B. B. Haab and R A. Mathies, Anal. Chern., 71, 5137 (1999)
17. J. Knerneyer, N. Marme and M. Sauer, Anai. Chern., n, 3717 (2000)
18. E. Y. Chan, N. M. Goncalves, R A. Haeusler, A. J. Hatch, J. W. Larson, A. M. Maletta, G. R. Yantz, E. D. Carstea, M. Fuchs, G. G. Wong, S. R. Gullans and R. Gilmanshin, Methods, 14, 1137 (2004)
19. Jonathan W. Larson, Gregory R. Yantz, Qun Zhong, Rebecca Charnas, Christina M. D'Antoni, Michael V. Gallo, Kimberly A Gillis, Lori A. Neely, Kevin M. Phillips, Gordon G. Wong, Steven R. Gullans, Rudolf Gilmanshin, Lab Chip, 2006, 6, 1187-1199
20. M. Foquet, J. Korlach, W. Zipfel, W. W. Webb and H. G. Craighead, Anal. Chern. 74, 1415 (2002)
21. H. P. Chou, C. Spence, A. Scherer and S. Quake, Proc. Natl. Acad. Sci. U.S.A., 96, 11 (1999)
22. R. Riehn, M. Lu, Y. Wang, S. F. Lim, E. C. Cox and R. H. Austin, Proc. Natl. Acad. Sci. U.S.A., 102, 10012 (2005)
23. J. T. Mannion, C. H. Reccius, J. D. Cross and H. G. Craighead, Biophysical Journal, 90, 4538 (2006)

24. S. W. Turner, P. M. Cabodi and H. G. Craighead, Phys. Rev. Lett., 88, 128103 (2002)
25. A van Orden, N. P. Machara, P. M. Goodwin and R. A. Keller, Anal. Chern., 70, 1444 (1998)
26. S. M. Stavis, J. B. Edel, Y. Li, K. T. Samiee, D. Luo and H. G. Craighead, Nanotechnology, 16, S314. (2005)
27. Michael Gosch, Hans B Jorn, Johan Holm, Toni Heino, Rudolf Rigler, Anal. Chern. 2000, 72, 32603265
28. P. M. Goodwin, R. L. Nolan and H. Cai, Current Pharmaceutical Biotechnology, 5, 271, (2004)
29. Haitao Li, Liming Ying, Jeremy J. Green, Shankar Balasubramanian, and David Klenerman, Anal. Chem. 2003, 75, 1664-1670
30. Haitao Li, Dejian Zhou, Helena Browne, Shankar Balasubramanian, and David Klenerman, Anal. Chem. 2004, 76, 4446-4451
31. Jerker Widengren, Volodyrnyr Kudryavtsev, Matthew Antonik, Sylvia Berger, Margarita Gerken, Claus A M. Seidel, Anal. Chem. 2006, 78, 2039-2050
32. Daekwang Kim, Yong-Geun Kwak, Seong Ho Kang, Analytica Chimica Acta, 577, 2006, 163-170
33. Johan Elf, Gene-Wei Li, X. Sunney Xie, Science, 316, 1191-1194, 2007
34. Aladdin Pramanik, Current Pharmaceutical Biotechnology, 5, 205-212, (2004)
35. Lingyan Li, Shengfu Chen, Seajin Oh, Shaoyi Jiang, Anal. Chem., 2002, 74, 6017-6022
36. Samuel M Stavis, Joshua B. Edel, Kevan T. Samiee, Harold G. Craighead, Lab Chip, 2005, 5, 337343
37. Antonie J. W. G. Visser, Beno H. Kunst, Hans Keller, Arjen Schots, Current Pharmaceutical Biotechnology, 2004, 5, 173-179
38. Amit Agrawal, Chunyang Zhang, Tyler Byassee, Ralph A. Tripp, Shuming Nie, Anal. Chem., 2006, 78, 1061-1070
39. Alonso Castro, John G. K. Williams, Anal. Chem. 1997, 69, 3915-3920
40. Chun-Yang Zhang, and Lawrence W. Johnson, Analyst, 2006, 131, 484-488-
41. X. Michalet, F. F. Pinaud, L. A. Bentolila, J. M. Tsay, S. Doose, J. J. Li, G. Sundaresan, A. M. Wu, S. S. Gambhir, S. Weiss, Science, 307, 2005, 539-544
42. Erin A S. Doherty, Robert J. Meagher, Methal N. Albarghouthi, Annelise E Barron., Electrophresis, 24, 34-53, 2003
43. F. Bedia Erim, Alejandro Cifuentes, Hans Poppe, Johan C. Kraak, Journal of Chromatography A, 708 (1995) 356-361
44. Zander, J. Enderlein, R. A Keller (Eds.), "Single Molecule Detection in Solution: Methods and Application", Chaper 3, Wiley-VCH, Germany, 2002
45. R. Rigler, E. S. Elson (Eds.), "Fluorsecence Correlation Spectroscopy: Theory and Applications", Springer, Berlin, Germany, 2001.
46. Invitrogen website, probes.invitrogen.com/resources/spectraviewer/

The invention claimed is:

1. A method comprising:
   (a) contacting a sample with a plurality of binding moieties that specifically bind a target molecule of the sample, wherein at least two binding moieties are bound to the same target molecule;
   (b) contacting the binding moieties bound to the target molecule with a plurality of detection moieties, which specifically bind to the binding moieties forming a detection complex, wherein the binding moieties are antibodies, which bind to multiple epitopes on the same target molecule, and the detection moieties are fluorophore-labeled antibodies;
   (c) introducing the sample containing the detection complex into a polyethylenimine (PEI)-coated channel of at least 100 nm in width; and
   (d) detecting the detection complex by 2D photon counting, using photon counts as a function of time from a single detection channel to determine single molecule or single complex detection.

2. The method of claim 1, at least three binding moieties are bound to the target molecule.

3. The method of claim 1, wherein the binding moieties are polyclonal antibodies.

4. The method of claim 1, wherein the fluorophore is a quantum dot or a fluorescent dye.

5. The method of claim 1, wherein the sample is a tissue or cell lysate.

6. The method of claim 1, wherein the target molecule comprises a protein, a nucleic acid or a protein or nucleic acid complex.

7. The method of claim 1, wherein the target molecule is a nucleic acid.

8. The method of claim 1, wherein the channel is at least 1 μm in width.

9. The method of claim 1, wherein the detection moieties comprise only one type of fluorophore.

10. The method of claim 6, wherein the target molecule is a protein complex, the method comprising contacting a sample with a plurality of binding moieties that specifically bind to at least two proteins in said protein complex, wherein at the least two binding moieties are separately bound to the at least two proteins in the complex.

\* \* \* \* \*

SEQUENCE LISTING

```
<160> NUMBER OF SEQ ID NOS: 11

<210> SEQ ID NO 1
<211> LENGTH: 761
<212> TYPE: PRT
<213> ORGANISM: Homo sapiens

<400> SEQUENCE: 1

Met Asp Ser Gly Gly Gly Ser Leu Gly Leu His Thr Pro Asp Ser Arg
1               5                   10                  15

Met Ala His Thr Met Ile Met Gln Asp Phe Val Ala Gly Met Ala Gly
            20                  25                  30

Thr Ala His Ile Asp Gly Asp His Ile Val Val Ser Val Pro Glu Ala
        35                  40                  45

Val Leu Val Ser Asp Val Val Thr Asp Asp Gly Ile Thr Leu Asp His
    50                  55                  60

Gly Leu Ala Ala Glu Val Val His Gly Pro Asp Ile Ile Thr Glu Thr
65                  70                  75                  80

Asp Val Val Thr Glu Gly Val Ile Val Pro Glu Ala Val Leu Glu Ala
                85                  90                  95

Asp Val Ala Ile Glu Glu Asp Leu Glu Glu Asp Asp Gly Asp His Ile
            100                 105                 110

Leu Thr Ser Glu Leu Ile Thr Glu Thr Val Arg Val Pro Glu Gln Val
        115                 120                 125

Phe Val Ala Asp Leu Val Thr Gly Pro Asn Gly His Leu Glu His Val
    130                 135                 140

Val Gln Asp Cys Val Ser Gly Val Asp Ser Pro Thr Met Val Ser Glu
145                 150                 155                 160

Glu Val Leu Val Thr Asn Ser Asp Thr Glu Thr Val Ile Gln Ala Ala
                165                 170                 175
```

```
Gly Gly Val Pro Gly Ser Thr Val Thr Ile Lys Thr Glu Asp Asp
            180                 185                 190

Asp Asp Asp Val Lys Ser Thr Ser Glu Asp Tyr Leu Met Ile Ser Leu
        195                 200                 205

Asp Asp Val Gly Glu Lys Leu Glu His Met Gly Asn Thr Pro Leu Lys
    210                 215                 220

Ile Gly Ser Asp Gly Ser Gln Glu Asp Ala Lys Glu Asp Gly Phe Gly
225                 230                 235                 240

Ser Glu Val Ile Lys Val Tyr Ile Phe Lys Ala Glu Ala Glu Asp Asp
                245                 250                 255

Val Glu Ile Gly Gly Thr Glu Ile Val Thr Glu Ser Glu Tyr Thr Ser
            260                 265                 270

Gly His Ser Val Ala Gly Val Leu Asp Gln Ser Arg Met Gln Arg Glu
        275                 280                 285

Lys Met Val Tyr Met Ala Val Lys Asp Ser Ser Gln Glu Glu Asp Asp
    290                 295                 300

Ile Arg Asp Glu Arg Arg Val Ser Arg Arg Tyr Glu Asp Cys Gln Ala
305                 310                 315                 320

Ser Gly Asn Thr Leu Asp Ser Ala Leu Glu Ser Arg Ser Ser Thr Ala
                325                 330                 335

Ala Gln Tyr Leu Gln Ile Cys Asp Gly Ile Asn Thr Asn Lys Val Leu
            340                 345                 350

Lys Gln Lys Ala Lys Lys Arg Arg Arg Gly Glu Thr Arg Gln Trp Gln
        355                 360                 365

Thr Ala Val Ile Ile Gly Pro Asp Gly Gln Pro Leu Thr Val Tyr Pro
    370                 375                 380

Cys His Ile Cys Thr Lys Lys Phe Lys Ser Arg Gly Phe Leu Lys Arg
385                 390                 395                 400

His Met Lys Asn His Pro Asp His Leu Met Arg Lys Lys Tyr Gln Cys
                405                 410                 415

Thr Asp Cys Asp Phe Thr Thr Asn Lys Lys Val Ser Phe His Asn His
            420                 425                 430

Leu Glu Ser His Lys Leu Ile Asn Lys Val Asp Lys Thr His Glu Phe
        435                 440                 445

Thr Glu Tyr Thr Arg Arg Tyr Arg Glu Ala Ser Pro Leu Ser Ser Asn
    450                 455                 460

Lys Leu Ile Leu Arg Asp Lys Glu Pro Lys Met His Lys Cys Lys Tyr
465                 470                 475                 480

Cys Asp Tyr Glu Thr Ala Glu Gln Gly Leu Leu Asn Arg His Leu Leu
                485                 490                 495

Ala Val His Ser Lys Asn Phe Pro His Val Cys Val Glu Cys Gly Lys
            500                 505                 510

Gly Phe Arg His Pro Ser Glu Leu Lys Lys His Met Arg Thr His Thr
        515                 520                 525

Gly Glu Lys Pro Tyr Gln Cys Gln Tyr Cys Ile Phe Arg Cys Ala Asp
    530                 535                 540

Gln Ser Asn Leu Lys Thr His Ile Lys Ser Lys His Gly Asn Asn Leu
545                 550                 555                 560

Pro Tyr Lys Cys Glu His Cys Pro Gln Ala Phe Gly Asp Glu Arg Glu
                565                 570                 575

Leu Gln Arg His Leu Asp Leu Phe Gln Gly His Lys Thr His Gln Cys
            580                 585                 590

Pro His Cys Asp His Lys Ser Thr Asn Ser Ser Asp Leu Lys Arg His
        595                 600                 605
```

-continued

```
Ile Ile Ser Val His Thr Lys Asp Phe Pro His Lys Cys Glu Val Cys
    610                 615                 620
Asp Lys Gly Phe His Arg Pro Ser Glu Leu Lys Lys His Ser Asp Ile
625                 630                 635                 640
His Lys Gly Arg Lys Ile His Gln Cys Arg His Cys Asp Phe Lys Thr
                645                 650                 655
Ser Asp Pro Phe Ile Leu Ser Gly His Ile Leu Ser Val His Thr Lys
            660                 665                 670
Asp Gln Pro Leu Lys Cys Lys Arg Cys Lys Arg Gly Phe Arg Gln Gln
        675                 680                 685
Asn Glu Leu Lys Lys His Met Lys Thr His Thr Gly Arg Lys Ile Tyr
690                 695                 700
Gln Cys Glu Tyr Cys Glu Tyr Ser Thr Thr Asp Ala Ser Gly Phe Lys
705                 710                 715                 720
Arg His Val Ile Ser Ile His Thr Lys Asp Tyr Pro His Arg Cys Glu
                725                 730                 735
Phe Cys Lys Lys Gly Phe Arg Arg Pro Ser Glu Lys Asn Gln His Ile
            740                 745                 750
Met Arg His His Lys Glu Ala Leu Met
        755                 760

<210> SEQ ID NO 2
<211> LENGTH: 2286
<212> TYPE: DNA
<213> ORGANISM: Homo sapiens

<400> SEQUENCE: 2
atggattcag gcggtggaag tcttggattg cacacgccag actctagaat ggcccatacc      60
atgattatgc aagattttgt ggctggaatg ctggtactg cacatatcga tggagaccat     120
attgttgttt cagttcctga agctgtttta gtttctgatg ttgtcacaga tgatgggata     180
actcttgatc atggccttgc agctgaagtt gtccatggac ctgatatcat cacagagact     240
gatgtagtaa cagaaggtgt gattgttcct gaagcggtac ttgaagctga tgttgccatt     300
gaagaggatt tagaggaaga tgatggtgat cacatcttga cttctgaact aattacagaa     360
accgttaggg taccagagca ggttttcgtg gctgaccttg ttactggtcc taatggacac     420
ttagaacatg tggtccaaga ttgtgtttca ggagtcgact ctcccacaat ggtatcagag     480
gaggttcttg taactaattc agatacagaa actgtgattc aagcagctgg aggtgttcct     540
ggttctacag ttactataaa aaccgaagat gatgatgatg atgatgtcaa gagcacttct     600
gaagactact aatgatatc tttgatgat gttggagaaa aattagagca tatgggaat     660 acaccattaa aaattggcag tgatggttca caagaagatg ctaaagaaga tgggtttggt     720
tctgaagtta taaagtgta tatatttaaa gcggaggctg aagatgatgt tgaaataggt     780
ggaacagaaa ttgtcacaga gagtgagtac accagtggac attcagtagc tggagtgctt     840
gaccagagcc gaatgcagcg ggagaagatg gtttacatgg cagttaaaga ttcttctcaa     900
gaagaagatg atatcagaga tgaaagaaga gtttcccgaa ggtatgaaga ttgtcaagca     960
tcaggaaata ctttggactc agcattagaa agcagaagta gtacagcagc acagtacctt    1020
caaatttgtg acggcattaa tacaaataaa gtacttaaac aaaaagccaa aagaggaga    1080 agggagaaa ccaggcagtg gcaaacagct gttataatag gtcctgatgg acagcccctc    1140
acagtgtacc cttgccatat ttgcacaaaa aagtttaaat ccaggggatt cttaaaaaga    1200
cacatgaaga atcatcctga tcatttaatg agaaaaaaat atcagtgtac agattgtgac    1260
```

-continued

```
tttacaacta acaagaaagt gagtttccat aaccacttag aaagccataa gctcataaac   1320
aaagtcgaca aaacccatga atttacagaa tacacacgaa gatacagaga ggctagtcca   1380
ctgagttcca ataaacttat tttaagagac aaggagccga agatgcacaa gtgcaaatac   1440
tgtgactatg aaactgcaga acaaggactg ttaaacaggc atttgttggc cgttcacagc   1500
aagaattttc ctcatgtttg tgttgagtgt gggaagggtt ttcgacatcc ttctgaactc   1560
aagaaacata tgagaaccca tactggtgag aagccatatc agtgtcagta ttgtattttc   1620
aggtgtgcag atcaatcaaa tctgaaaact cacattaagt ctaaacatgg taacaatttg   1680
ccatataaat gtgagcattg tccccaagca tttggtgatg agagggagct caacgccat    1740 ctggatttgt ttcaaggaca taagacacac cagtgtcctc attgtgacca taagagcacc   1800
aattcaagtg accttaagcg gcacatcata tctgtccata ctaaggattt tcctcacaaa   1860
tgtgaggtct gtgataaagg ttttcatcgt ccttctgagc tcaaaaagca tagtgatatc   1920
cataagggta ggaagattca tcagtgcagg cactgtgact ttaaaacatc cgatccattt   1980
attcttagtg gccatatcct ttcagttcat actaaagatc agccattgaa atgtaaaagg   2040
tgcaagagag gattcagaca acaaaatgag ctaaaaaaac atatgaagac ccatactgga   2100
aggaagattt accaatgtga gtattgtgaa tacagcacta cagatgcatc tggctttaaa   2160
cgacatgtga tatcaataca tacaaaagac tatccacaca ggtgtgaatt ctgcaagaag   2220
ggattccgaa gaccatcaga aaaaaatcag catattatga ggcaccacaa agaggctctt   2280
atgtaa                                                             2286
```

<210> SEQ ID NO 3
<211> LENGTH: 22
<212> TYPE: RNA
<213> ORGANISM: Artificial Sequence
<220> FEATURE:
<223> OTHER INFORMATION: Synthetic primer

<400> SEQUENCE: 3
acuguugcua auaugcaacu cu                                              22

<210> SEQ ID NO 4
<211> LENGTH: 23
<212> TYPE: RNA
<213> ORGANISM: Artificial Sequence
<220> FEATURE:
<223> OTHER INFORMATION: Synthetic primer

<400> SEQUENCE: 4
uacccuguag auccgaauuu gug                                             23

<210> SEQ ID NO 5
<211> LENGTH: 22
<212> TYPE: RNA
<213> ORGANISM: Artificial Sequence
<220> FEATURE:
<223> OTHER INFORMATION: Synthetic primer

<400> SEQUENCE: 5
ucgugucuug uguugcagcc gg                                              22

<210> SEQ ID NO 6
<211> LENGTH: 22
<212> TYPE: RNA
<213> ORGANISM: Artificial Sequence
<220> FEATURE:
<223> OTHER INFORMATION: Synthetic primer

```
<400> SEQUENCE: 6
aacuguuugc agaggaaacu ga                                              22

<210> SEQ ID NO 7
<211> LENGTH: 21
<212> TYPE: RNA
<213> ORGANISM: Artificial Sequence
<220> FEATURE:
<223> OTHER INFORMATION: Synthetic primer

<400> SEQUENCE: 7
uugugcuuga ucuaaccaug u                                               21

<210> SEQ ID NO 8
<211> LENGTH: 23
<212> TYPE: RNA
<213> ORGANISM: Artificial Sequence
<220> FEATURE:
<223> OTHER INFORMATION: Synthetic primer

<400> SEQUENCE: 8
uacccuguag aaccgaauuu gug                                             23

<210> SEQ ID NO 9
<211> LENGTH: 22
<212> TYPE: RNA
<213> ORGANISM: Artificial Sequence
<220> FEATURE:
<223> OTHER INFORMATION: Synthetic primer

<400> SEQUENCE: 9
ugccugucua cacuugcugu gc                                              22

<210> SEQ ID NO 10
<211> LENGTH: 22
<212> TYPE: RNA
<213> ORGANISM: Artificial Sequence
<220> FEATURE:
<223> OTHER INFORMATION: Synthetic primer

<400> SEQUENCE: 10
ugggucuuug cgggcgagau ga                                              22

<210> SEQ ID NO 11
<211> LENGTH: 22
<212> TYPE: RNA
<213> ORGANISM: Artificial Sequence
<220> FEATURE:
<223> OTHER INFORMATION: Synthetic primer

<400> SEQUENCE: 11
ggcuggcucg cgaugucugu uu                                              22
```